(12) United States Patent
Biscup et al.

(10) Patent No.: US 7,883,532 B2
(45) Date of Patent: Feb. 8, 2011

(54) VERTEBRAL PARS INTERARTICULARIS CLAMP A NEW SPINE FIXATION DEVICE, INSTRUMENTATION, AND METHODOLOGY

(75) Inventors: Robert S. Biscup, Fort Lauderdale, FL (US); Clayton G. Leroux, Westlake, OH (US)

(73) Assignee: Spineco, Inc., Westlake, OH (US)

( * ) Notice: Subject to any disclaimer, the term of this patent is extended or adjusted under 35 U.S.C. 154(b) by 632 days.

(21) Appl. No.: 11/405,203

(22) Filed: Apr. 17, 2006

(65) Prior Publication Data

US 2006/0241591 A1    Oct. 26, 2006

Related U.S. Application Data

(60) Provisional application No. 60/674,426, filed on Apr. 25, 2005.

(51) Int. Cl.
    *A61B 17/70*    (2006.01)
    *A61B 17/84*    (2006.01)

(52) U.S. Cl. .................. 606/324; 606/246; 606/330

(58) Field of Classification Search ............ 606/324, 606/330; D24/143; D8/72–74
See application file for complete search history.

(56) References Cited

U.S. PATENT DOCUMENTS

| | | | |
|---|---|---|---|
| 4,107,480 A | 8/1978 | Schlichte | |
| 5,882,350 A | 3/1999 | Ralph | |
| 5,989,254 A | 11/1999 | Katz | |
| 5,997,539 A | 12/1999 | Errico | |
| 6,004,322 A | 12/1999 | Bernstein | |
| 6,004,349 A | 12/1999 | Jackson | |
| 6,017,344 A | 1/2000 | Errico | |
| 6,053,917 A | 4/2000 | Sherman | |
| 6,056,753 A | 5/2000 | Jackson | |
| 6,083,227 A | 7/2000 | Saurat | |
| 6,113,601 A | 9/2000 | Tatar | |
| 6,183,472 B1 | 2/2001 | Lutz | |
| 6,224,596 B1 | 5/2001 | Jackson | |
| 6,368,319 B1 | 4/2002 | Schaefer | |
| 6,375,675 B2 | 4/2002 | Dehdashtian | |
| 6,402,752 B2 | 6/2002 | Schaffler-Wachter | |
| 6,451,019 B1* | 9/2002 | Zucherman et al. | 606/324 |
| 2003/0109881 A1* | 6/2003 | Shirado et al. | 606/61 |

\* cited by examiner

*Primary Examiner*—Eduardo C Robert
*Assistant Examiner*—Julianna N Harvey
(74) *Attorney, Agent, or Firm*—Fay Sharpe LLP; Brian E. Turung

(57) ABSTRACT

An improve spinal surgical implant used primarily in the posterior aspect of the spinal column for spinal reconstruction; revision surgery; deformity correction; and/or tumor surgery and/or trauma surgery of the cervical, thoracic and/or and lumbo-sacral spine.

25 Claims, 9 Drawing Sheets

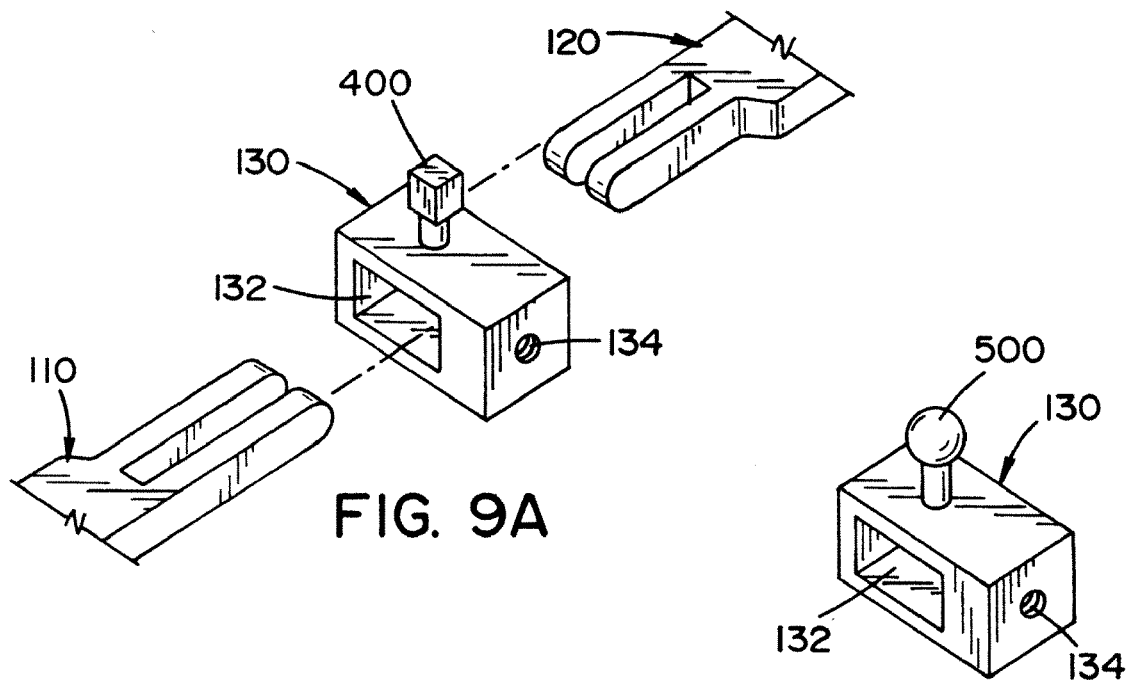
FIG. 9A
FIG. 9B
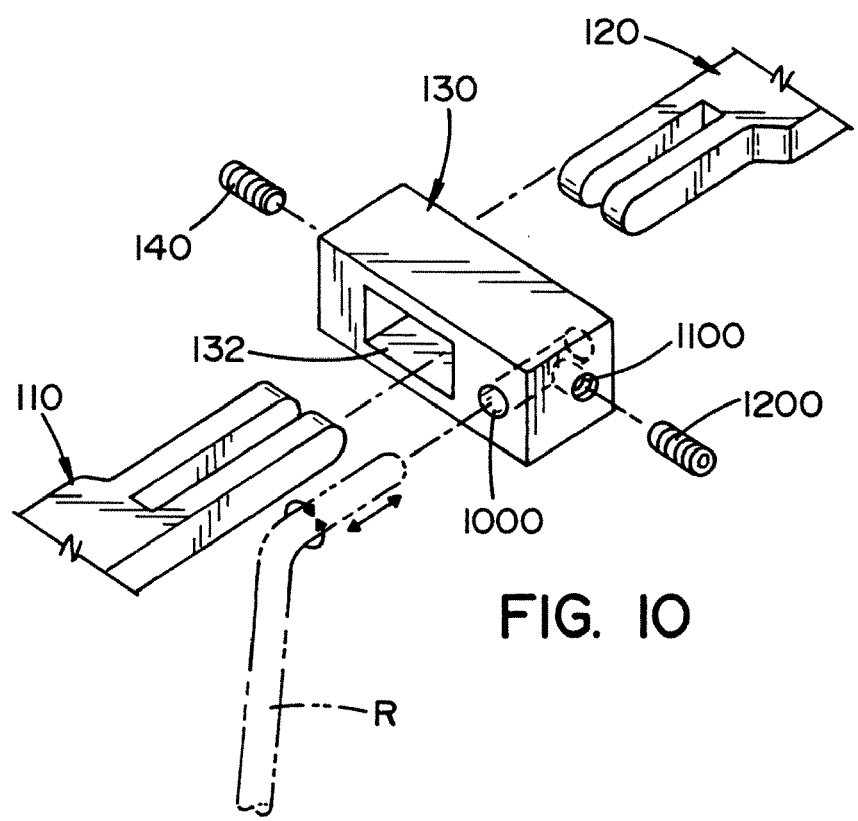
FIG. 10

VERTEBRAL PARS INTERARTICULARIS CLAMP A NEW SPINE FIXATION DEVICE, INSTRUMENTATION, AND METHODOLOGY

The present invention claims priority on co-pending U.S. Provisional Application Ser. No. 60/674,426 filed Apr. 25, 2005, which is incorporated herein by reference.

The present invention is directed to implants, more particularly to spinal implants, and even more particularly to a device and method for using a device that is designed to secure to the spinal column.

BACKGROUND OF THE INVENTION

The human spine is made up of a column of thirty-three bones and their adjoining structures. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs forms a central axis that supports the head and torso. These vertebrae also enclose an opening through which the spinal cord passes.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compression of the neural structures, causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine due to the relatively large number of vertebrae, the minor loss of mobility is typically acceptable.

For the replacement of a vertebra of the human spinal column, for the distraction of the spinal column, for the stabilization of the vertebrae and likewise, it is known to apply pedicle screws. The pedicle screw is screwed into the pedicle of the vertebra and the head of the pedicle screw is connected to suitable provisions, for example to a stabilizing system, to distraction rods, etc. During the treatment of the spine, the pedicle screw is generally first rotated into the pedicle. Subsequently, the insertion of the rod is effected.

A standard pedicle screw assembly comprises a screw having an externally threaded stem having in turn a head provided with parts allowing it to be secured to one end of a distraction rod. Typically two such pedicle screws are inserted into respective vertebrae and are secured to a rod to distract and/or stabilize a spinal column after, for instance, a disk operation. One commonly used pedicle screw is disclosed in German Patent No. 4,107,480, which is incorporated herein by reference, and includes a head that has a pair of outwardly projecting parallel ridges with overhanging inner edges. A cap formed with a pair of complementary inwardly open slots fits with these ridges. The pedicle screw is threaded into the vertebrae, an end of the rod is fitted to its outer end, the cap is then slid transverse to the pedicle screw axis and parallel to the rod, over the rod to capture it, and finally a cap screw threaded into the cap and tightened to press the rod down against the head of the pedicle screw and thereby fix the rod, cap, and screw together. Many other pedicle screw designs have been developed to simplify the insertion of the pedicle screw into the pedicle, and/or to reduce damage to the pedicle screw and/or the pedicle during surgery. Some of these pedicle screw designs are disclosed in U.S. Pat. Nos. 5,882,350; 5,989,254; 5,997,539; 6,004,322; 6,004,349; 6,017,344; 6,053,917; 6,056,753, 6,083,227; 6,113,601; 6,183,472; 6,224,596; 6,368,319; 6,375,657; and 6,402,752; and the patents cited and disclosed in such patents. All these designs of pedicle screws are incorporated herein by reference.

After the pedicle screw is inserted in the pedicle, the bone around the pedicle screw must heal to properly secure the pedicle screw in the bone. Any infection that occurs around the pedicle screw can slow the healing process and/or damage the bone around the pedicle screw thereby weakening the connection between the bone and pedicle screw. Typically, a patient is given antibiotics for several days after the surgery to reduce the occurrence of infection about the pedicle screw. The patient may also receive electrical stimulation during surgery to promote the healing process of the bone about the pedicle screw. Both of these techniques have improved the post-operative success of the surgical procedure; however, improved success rates are still needed.

Although the use of pedicle screws are successfully used in a variety of surgical techniques, there are instances wherein the use of the pedicle screw may unnecessarily damage the bone. For instance, a particular vertebra may be too small, too fragile, partially damaged, etc. to accept a pedicle screw. As such, a particular spinal procedure cannot be performed by use of pedicle screws. Situations also arise in that the orientation of the pedicle screw in the vertebrae is awkward, thereby complicating a spinal procedure that involves the connection of one or more other components to the pedicle screw.

In view of these situations, there is a need for a device that can be secured to one or more vertebrae which device does not need to damage or otherwise penetrate into a vertebra and which device can be used to connect to other components of a stabilizing system, to distraction rods, etc.

SUMMARY OF THE INVENTION

The present invention is directed to a spinal implant, and particularly to a spinal implant used primarily in the posterior aspect of the spinal column for spinal reconstruction; revision surgery; deformity correction; and/or tumor surgery and/or trauma surgery of the cervical, thoracic and/or and lumbosacral spine surgery; however, it will be appreciated that the implant can be used in other regions of the spine and/or for use in other or additional applications.

In one non-limiting aspect of the invention, the spinal implant is designed to secure to one or more spinal vertebrae without having to penetrate or substantially penetrate into the vertebrae. In one non-limiting embodiment of the invention, the spinal implant is configured to at least partially clamp to one or more portions of a vertebra. This clamping configuration enables the spinal implant to be connected to one or more vertebrae without having to penetrate into the one or more vertebrae. As such, the spinal implant does not require drilling of insertion holes into the vertebrae, which insertion holes can i) cause damage to the vertebrae (e.g., fracturing and/or splitting of the vertebrae, etc.), and ii) require healing of the vertebrae about the device that has been inserted into the hole in the vertebrae prior to securing a stabilizing system, to distraction rods, etc. to the inserted device, thereby increasing procedure times and/or inconvenience to the patient.

In one non-limiting aspect of the present invention, the spinal implant is in the form of a "clamp" which is designed to be applied to the posterior elements of one or more spinal vertebrae. In one non-limiting embodiment of the invention, the spinal implant includes two or more legs or arms that are used to at least partially secure the spinal implant to one or more vertebra. One or more of the arms or legs can be adjustable; however, this is not required. One or more of the arms or legs can include a grasping portion or foot portion that is used to at least partially engage and secure at least a portion of the arm or leg to the one or more vertebra. In one non-limiting aspect of this embodiment, the spinal implant includes two arms or legs. In another and/or alternative non-limiting aspect of this embodiment, the grasping portion includes an angulated section at an end portion of one or more of the arms or legs. This angulated section deviates by at least about 20° from the planar, generally a planar or slightly curved profile of the arm or legs of the spinal implant. In one non-limiting design, the angulated section is designed to at least partially hook onto a portion of one or more vertebra. In still another and/or alternative non-limiting aspect of this embodiment, one or more of the arms or legs can include one or more engaging structures (e.g., teeth, ribs, non-smooth surfaces, etc.) that are used to facilitate in engaging a portion of the arms or legs to a portion of one or more vertebra.

In another and/or alternative non-limiting aspect of the present invention, the spinal implant is designed to be at least partially clamped within the interval between the superior margin of the lamina of a vertebra and the lateral margin of the pars interarticularis portion of the vertebra. In one non-limiting embodiment of the invention, the spinal implant is designed to span at least a portion of the length of the pars interarticularis of the vertebra. In one non-limiting aspect of this embodiment, the spinal implant is designed to span a portion of the length of the pars interarticularis of the vertebra. In another non-limiting aspect of this embodiment, the spinal implant is designed to span the full length of the pars interarticularis of the vertebra. In still another non-limiting aspect of this embodiment, the spinal implant is designed to span more than one vertebra (e.g., two vertebra, three vertebra, etc.). In yet another non-limiting aspect of this embodiment, the spinal implant is designed to be formed into a pedicle "claw" to enable the spinal implant to be affixed to a vertebra if the lamina or pars has been removed. In this non-limiting design, the spinal implant can create a different configuration of the pedicle "clamp" with the clamping of the superior and inferior walls of the pedicle. In accordance with these non-limiting aspects of the invention, the spinal implant is designed to provide a strong and secure permanent or temporary fixation to the posterior elements of a vertebra or to multiple vertebrae. The spinal implant is also designed to allow for one or more attachments to be placed upon and/or connected to the spinal implant, thus functioning in part as a platform and/or docking station for one or more other components that are used to address one or more spinal issues and/or one or more issues located near the spine.

In still another and/or alternative non-limiting aspect of the invention, the spinal implant is designed to simplify spinal procedures and/or facilitate the improvement of the patient's health in that the spinal implant can facilitate in partially replacing or eliminating the need for lamina and transverse process hooks, pedicle screws, sub-laminar wires, and/or spinous process buttons. The spinal implant is believed to be especially useful in medical procedures involving the young and aging spine alike since the spinal implant can improve and, in most cases, provide a strong, if not the strongest, fixation possible in comparison to other devices which can have a higher percentage of failure.

In yet another and/or alternative non-limiting aspect of the invention, the spinal implant can be used in a variety of spinal procedures. A few non-limiting examples of the potential use and applications of the spinal implant include, but are not limited to, Scoliosis surgery (e.g., Pediatric, Adult, Geriatric (i.e., "Aged"), Degenerative, Post Surgery, etc.); Degenerative Spine Conditions; Spine Fractures; Tumors; Small Pedicles that cannot be or are difficult to be accessed by a pedicle screw; Repair of Spondylolysis (Pars Defects); and/or Bone Anchor for an "artificial facet" type implant. As can be appreciated, other or additional applications of the spinal implant can be appreciated.

In yet another and/or alternative non-limiting aspect of the invention, the spinal implant can include one or more of the following components: 1) a fixed or adjustable medial lamina clamp and/or foot (e.g., first clamp arm, etc.); 2) an adjustable hinged (or otherwise articulated) pars clamp and/or foot which (e.g., a lateral pars clamp and/or foot, etc.) (e.g., second clamp arm, etc.); 3) a set-screw and/or locking nut or other device or mechanical means for adjustments and/or tightening one or more components of the spinal implant; 4) an integral base (e.g., arm hub, etc.) which can include one or more docking stations—which may be threaded and/or constructed with another coupling device or mechanism; 5) one or more fixed and/or variable motion attachments that are at least partially designed to connected to one or more other components of a stabilizing system and/or other type of treatment system (e.g., modular heads; one or more attachment sites for rods, plates, and/or medication delivery devices, etc.); 6) one or more smooth surfaces, 7) one or more surfaces that are coated with one or more materials (e.g., medicines and/or drugs, adhesives, proteins, cells, antibodies, etc.); 8) one or more porous regions to allow for bone ingrowth into the clamp to facilitate in providing a permanent bond between the implant the spinal lamina and/or to allow for fluid flow (e.g., body fluids, medicine, drugs, cells, etc.) into and/or out of the spinal implant; and/or 9) one or more cross links connect to at least one side of a vertebra to another vertebra (e.g., force coupling) by use of one or more fixed or flexible couplers (i.e., cross links could connect single or multiple levels of vertebral bodies, etc.).

In still yet another and/or alternative non-limiting aspect of the invention, the spinal implant can be manufactured in variable sizes to better meet the needs of the particular patient's anatomy.

In a further and/or alternative non-limiting aspect of the present invention, the spinal implant can be constructed of a single material or from a combination of materials. Non-limiting materials that can be used to fully or partially form the spinal implant include, but are not limited to, metals, alloys, ceramics, polymers, plastics, memory metals, HA, fiber reinforced materials, mammalian bone, cartilage and/or other appropriate materials. The material used to form one or more portions of the spinal implant can be porous or non-porous, coated and/or non-coated. The material can include a bioactive and/or bioinert material. The material can be bioabsorbable or non-bioabsorbable. The material can include one more medicines or drugs. The spinal implant can also or alternatively include one or more drugs, medicine and/or other osteobiologics (e.g., BMPs, bone marrow concentrate, fillers, medicine, one or more biological agents, substitutes, etc.). The one or more drugs, medicine and/or other osteobiologics can thus form at least a portion of the spinal implant, be imbedded in at least a portion of the spinal implant and/or be coated on at least a portion of the spinal implant. As can be appreciated, different concentrations and/or different types of one or more drugs, medicine and/or other osteobiologics can be located on different portions of the spinal implant.

In yet a further and/or alternative non-limiting aspect of the present invention, the spinal implant can be designed to permanently or detachably connect to a "Lamina Plate." A Laminal Plate can be attached so as to replace or reconstruct the lamina or posterior wall of the spinal column. Such a Lamina Plate can include one or more smooth and/or porous regions, and can, among other goals, connect the spinal implant (e.g., right side, left side, etc.).

In still yet another and/or alternative non-limiting aspect of the present invention, the spinal implant can be constructed with low profile features so as to inhibit or prevent possible injury and/or damage to neurological elements adjacent or near the spinal implant.

In a further and/or alternative non-limiting aspect of the present invention, the spinal implant can be used in conjunction with innovative instrumentation to facilitate the preparation of the surgical site, the insertion of the spinal implant, the revisitation to the surgical site, and/or the attachment/disconnection of one or more components to the spinal implant device. Non-limiting examples of such innovate instruments include, but are not limited to, 1) An Inserter-Manipulator-Tightener which can be a single instrument or a set of instrument, 2) Exposure instrument(s), 3) Site prep instrument(s), 4) Inserter/remover instrument(s), and/or 5) Trial or sizing device(s). As can be appreciated, other or additional instruments can be used in conjunction with the spinal implant.

In still a further and/or alternative non-limiting aspect of the present invention, the spinal implant can include a "Third Foot" attachment for 3-point fixation to one or more vertebra. Such a "Third Foot" arrangement can also be referred to as "The Long Arm" attachment of the spinal implant. In one non-limiting embodiment of the invention, the third arm is designed to be adjustably positionable. In this particular aspect of the invention, the third arm is able to be moveably positioned to a desired location to facilitate in securing the spinal implant to one or more vertebra. The length of the third can be selected so that the third is securable to the same vertebra as the first and second arm, or the third arm can have a length to secure to a vertebra other than the vertebra that the first and second arm are secured to. In another and/or alternative embodiment, third arm can be designed to be secured or locked in positioned once the third arm is properly oriented. The locking or securing arrangement can be accomplished by a variety of means such as, but not limited to, bolts, locking teeth, clamp, ribs, slots, screws, pins, etc.

In yet a further and/or alternative non-limiting aspect of the present invention, the spinal implant can be configured so as to address the various needs of different portions of the mammalian spine, including but not limited to, cervical, thoracic, and lumbar-sacral" versions.

In still yet a further and/or alternative non-limiting aspect of the present invention, the spinal implant can be designed to span more than one segment if one or more pars has been removed.

In another and/or alternative non-limiting aspect of the present invention, the spinal implant can include a cap and/or other device to cover one or more openings in the spinal implant to 1) facilitate the revisitation to the spinal implant, 2) for the purpose of changing the one or more attachments and/or attachment methodology on the spinal implant, and/or 3) inserting and/or removing one or more drugs, medication, etc. in one or more cavities in the spinal implant. The cap, when used, can be made of one or more materials including, but not limited to, plastic, metal, etc. The cap can be biodegradable or non-biodegradable. The cap can include a threaded and/or other connection arrangement to permanently or removably secure the cap to the spinal implant.

In still another and/or alternative non-limiting aspect of the present invention, the spinal implant can be designed so that a surgical site, the vertebra and/or the spinal implant can be re-visited from time to time as necessary. This capability can be instrumental in the future success of motion preservation implants (such as the concept of an artificial facet which would be designed and manufactured to be attached to a vertebra).

In yet another and/or alternative non-limiting aspect of the present invention, the spinal implant can be designed to attach to the laminar portion of a vertebra for purposes of surgical treatment of a spinal condition.

In still yet another and/or alternative non-limiting aspect of the present invention, the spinal implant can be designed to attach to two adjacent vertebrae for purposes of surgical treatment of a spinal condition.

In a further and/or alternative non-limiting aspect of the present invention, the spinal implant can be designed to attach to two vertebrae' laminae.

In still a further and/or alternative non-limiting aspect of the present invention, the spinal implant can be designed to clamp onto at least a portion of the vertebral body by gripping onto the natural faces of the vertebra.

In still yet a further and/or alternative non-limiting aspect of the present invention, the spinal implant can be designed to utilize a locking nut and/or other type of mechanism to affix, position and/or disconnect the spinal implant to the one or more vertebra.

In another and/or alternative non-limiting aspect of the present invention, the spinal implant can be designed to utilize a hinged and/or articulated device to attach to one or more vertebral bodies, or a portion thereof.

In still another and/or alternative non-limiting aspect of the present invention, the spinal implant can be designed to utilize a capping or covering device to cover one or more access ports of the surgical implant to keep the access port clear and/or avoid tissue ingrowth. The capping or covering device can be removable or non-removable. The capping or covering device can be biodegradable or non-biodegradable.

In yet another and/or alternative non-limiting aspect of the present invention, the spinal implant can be designed to form an artificial facet onto a vertebral body to facilitate in improving a patient's spinal function.

In still yet another and/or alternative non-limiting aspect of the present invention, the spinal implant can be used in a variety of methodologies. One non-limiting methodology that can include the use of the spinal implant includes 1) Performing at least one exposure procedure to access/prepare at least a portion of a surgical site (e.g., Surgical exposure via open or minimally-invasive surgery ("MIS") approach, Preparing surface for bio-ingrowth; Small laminotomy, if necessary, in superior lamina, small laminotomy, if necessary, in lateral pars; etc.), 2) Determining the proper size of the spinal implant, 3) Positioning/securing the spinal implant to one or more vertebra, and 4) Connecting one or more components (e.g., third arm of the spinal implant, universal connector, modular connection head, connection extension, cross-link, rod, plate, motion preservation device, medicine/drug delivery device, electro-simulation device, etc.) to the spinal implant. As can be appreciated, many modifications of this methodology can be used in conjunction with the spinal implant. One non-limiting specific methodology that can include the use of the spinal implant, such non-limiting methodology includes 1) Performing at least one an exposure procedure to access/prepare at least a portion of the spine, 2) Determining the proper size of the spinal implant, 3) Securing the spinal implant to one or more vertebra, 4) Positioning/securing one or more components of the spinal implant for optimum fixation and position on one or more vertebra, 5) Reviewing position of the spinal implant (e.g., MIS review, radiological review, visual review, etc.), and 6) Connecting one or more components to the spinal implant. In another and/or alternative non-limiting specific methodology that can include the use of the spinal implant, such non-limiting methodology includes 1) Performing at least one an exposure procedure to access/prepare at least a portion of the spine, 2) Determining the proper size of the spinal implant, 3) Positioning/securing the spinal implant to one or more vertebra (e.g., engaging the medial lamina foot of spinal implant on a vertebra, next engaging the lateral pars foot of the spinal implant on the same or different vertebra, secure/tighten the feet of the spinal implant to the one or more vertebra (e.g., close or tighten clamp or other type of tightening mechanism across pars, etc.), etc.), 4) Manipulating/adjusting the position of the spinal implant on the vertebra and/or one or more components of the spinal implant to obtain the desired fixation and/or position of the spinal implant on the one or more vertebra, 5) Reviewing position of the spinal implant on the one or more vertebra, 6) Performing final tightening/positioning of the spinal implant on the one or more vertebra, 7) Repeating the above steps for the connection of one or more other spinal implants on the same or different vertebra, and 8) Connecting one or more components to the spinal implant. As can be appreciated, other or additional methodologies can be used with the spinal implant of the present invention.

In still yet another and/or alternative non-limiting aspect of the present invention, the spinal implant can provide one or more of the following benefits: 1) Eliminates the need for a hospital or other medical facility to carry a large inventory of lamina hooks, wires, screws, buttons, etc.; 2) Enhances fixation to a vertebral body or multiple vertebral bodies (e.g., clamp design, cortical bone, etc.); 3) Allows for force coupling of the construct, if desired, for enhanced purchase and better control for manipulating the vertebra body and motion segment (deformity surgery); 4) Allows for bio-ingrowth capability for permanent fixation to lamina biologically; 5) Allows for the attachment of growth rods for pediatric scoliosis; 6) Provides a method of addressing the disease of Osteoporosis; 7) Facilitates in Motion Preservation in the spine, as compared to alternative surgical methodologies; 8) Allows Revision Surgery to be undertaken with greater ease than current devices; 9) Provides "lamina prosthesis" for repair or reconstruction surgery; 10) Creates or permits the formation of a permanent "docking" site that can be revisited by the surgeon or a subsequent surgeon; 11) Permits the ability to control vertebral motion or manipulation such as, but not limited to e-Rotation, 3-D contouring, etc.; 12) Provides similar advantages to standard pedicle screw fixation; 13) Allows for Uni or bilateral control or fixation; 14) Allows for Single or Multi-level construct using "links"; 15) Provides a substitute for pedicle screws (thus target surgeons that might be "squeamish" on using pedicle screws); 16) Provides a substitute for pedicle screws when pedicle screw usage is impractical (e.g., small, osteoporotic, missing pedicle, etc.); 17) Provides a replacement for pedicle screw prosthesis or, in the alternative, can be used to complement the pedicle screw prosthesis implant system; 18) Can be attached to or be used with pedicle screw instrumentation; 19) Can be attached to or be used with artificial vertebral body implant (e.g., 360°) reconstruction; 20) Can be created and/or be modified utilizing injection molding technology for customization; and/or 21) Can be staged using MIS approach for bio-ingrowth application, such as surgically inserting a sleeve into the site and, later, inserting this device into the fixed sleeve site. As can be appreciated, the spinal implant can have other or additional benefits.

In a further and/or alternative non-limiting aspect of the present invention, the spinal implant can be used in a variety of treatments. Some of the diseases the spinal implant can be used to help in the treatment of include, but are not limited to: 1) Tumors, 2) Infections, 3) Revision surgery, and/or 4) Trauma.

In still a further and/or alternative non-limiting aspect of the present invention, the spinal implant can be designed for bio-ingrowth. A Bio-ingrowth version of the spinal implant can be used with motion preservation devices by providing a solid fixation point to the bone—minimizes loosening, and/or stress shielding and maximizes load sharing.

In summary, the spinal implant is a new and innovative spine implant that can be used be used primarily in the posterior aspect of the spinal column for spinal reconstruction, revision surgery, deformity correction, tumor, and trauma surgery of the cervical, thoracic, and lumbo-sacral spine. The spinal implant can be designed to removably or irremovably "clamp" or secure onto the posterior elements of one or more spinal vertebrae. In one non-limiting embodiment, the spinal implant can be clamped within the interval between the superior margin of the lamina of a vertebra and the lateral margin of the pars interarticularis portion of the vertebra. The spinal implant can be designed to span the length of the pars interarticularis, or, secondarily, a portion thereof or, in the alternative, more than one vertebra's surface. The spinal implant, when secured to one or more vertebra, can provide strong permanent or temporary fixation to the posterior elements of a vertebra or multiple vertebrae and allow for a variety of attachments to be placed upon and/or connected to the spinal implant, thus functioning a platform and/or docking station for one or more other components. The spinal implant is envisioned to simplify spinal procedures and/or facilitate the improvement of the patient's health in that it can replace the need for lamina and transverse process hooks, pedicle screws, sub-laminar wires, and/or spinous process buttons. The primary market for the spinal implant is believed to be for the young and aging spine alike since the spinal implant is believed to provide improved and, in most cases, the strongest fixation possible in comparison to other devices which can have a high percent of failure. The spinal implant is believed to be usable to assist in Scoliosis surgery (e.g., Pediatric, Adult, Geriatric), Degenerative Post Surgery, Degenerative Spine Conditions, Spine Fractures, Tumors, Small Pedicles that cannot be accessed by a pedicle screw, Repair of Spondylolysis (Pars Defects), and/or a Bone Anchor for an "artificial facet" type implant. The spinal implant may have other uses. The spinal implant can be formed into a clamp-type device.

When the spinal implant is a clamp-type device, the spinal implant can include one or more of the following components: 1) A fixed medial lamina clamp and/or foot; 2) An adjustable hinged (or otherwise articulated) pars clamp and/or foot which, in its primary embodiment, will be a lateral pars clamp and/or foot; 3) A set-screw or locking nut or other device or mechanical means for adjustments and/or tightening; 4) An integral base which might include docking station—which may be threaded or constructed with another coupling device or mechanism; 5) A variety of fixed and/or variable motion attachments to the docking station which might consist of, for example, Modular heads (see pedicle prosthesis system), Attachment sites for rods, plates, medication delivery devices, etc.; 6) Smooth or porous surfaces, coated which may be coated with an appropriate substance or not—If constructed with a porous surface, this would allow bone in-growth into the clamp providing a permanent bond between the implant the spinal lamina. The intent is that the surgical site, the vertebra and/or the clamp can be re-visited from time to time as necessary. This capability can be critical to the future success of motion preservation implants (such as the concept of an artificial facet which would be designed and manufactured to be attached to a vertebra); and/or 7) Cross Links to connect right to left side of one vertebra to another (force coupling) by means of fixed or flexible couplers. In this regard, it is contemplated that cross links could connect single or multiple levels of vertebral bodies. The spinal implant could also be designed as a pedicle "claw" to enable the device to be affixed to a vertebra if the lamina or pars has been removed). This design could create a different configuration of the pedicle "clamp" with the clamping of the superior and inferior walls of the pedicle. The spinal implant could be manufactured in variable sizes to better meet the needs of the particular patient's anatomy. The spinal implant can be constructed of a single material or of a combination of materials. Such materials could include metals, alloys, ceramics, plastics, memory metals, mammalian bone, cartilage and/or other appropriate materials. One or more spinal implants can be used in conjunctions with a "Lamina Plate." The "Lamina Plate" can be attached to one or more vertebra so as to replace or reconstruct the lamina or posterior wall of the spinal column. Such a "Lamina Plate" could be smooth or porous. The"Lamina Plate" could be designed to connect to a one spinal implant or to a plurality of spinal implants. The spinal implant can be constructed with a low profile foot to minimize possible injury to the neurological elements adjacent or near the spinal implant. Innovative instrumentation can be used with the spinal implant to facilitate in the preparation of the surgical site, the insertion of the spinal implant, the revisitation to the surgical site, and/or the attachment of one or more components to the spinal implant. Some of these innovative instruments can include 1) An "Inserter-Manipulator-Tightener" which is envisioned as an All-in-one concept or, if appropriate, in multiple components, 2) Exposure instrument(s), 3) Site prep instrument(s), 4) Inserter/remover instrument(s), and/or 5) Trial or sizing device(s). The spinal implant can include a "Third Foot" attachment for enhanced 3-point fixation (e.g., "A Long Arm" attachment). As can be appreciated, the spinal implant could include four or more feet. The spinal implant can be configured in one or more designs so as to address the various needs of different portions of the mammalian spine, including but not limited to cervical, thoracic, and lumbar-sacral" versions. The spinal implant can be design to span more than one segment if pars has been removed. The spinal implant can include one or more caps or other devices to at least partially cover one or more openings in the spinal implant. These one or more openings can be used to facilitate in the revisitation to the spinal implant, facilitate in changing the attachment arrangement and/or methodology of the spinal implant, facilitate in connecting one or more components to the spinal implant, and/or receive one or more medicine or drugs. The cap can be made of one or more materials including plastic, metal, etc. The cap can be threaded or connected to the spinal implant by one or more mechanical methodologies. The spinal implant can be designed to attach to the laminar portion of a vertebra for purposes of surgical treatment of a spinal condition. The spinal implant can be designed to onto two adjacent vertebrae for purposes of surgical treatment of a spinal condition. The spinal implant can be designed to attach to two vertebrae laminae. The spinal implant can be designed to clamp onto the vertebral body by gripping onto the natural faces of the vertebra. The spinal implant can be designed to include a locking nut or device to affix the spinal implant onto the vertebra. The spinal implant can be designed to include a hinged or articulated structure for use in attaching the spinal implant to a vertebral body, or a portion thereof. The spinal implant can be designed to include a capping device to cover one or more access ports of the spinal implant to keep the access port clear and/or avoid tissue ingrowth. The spinal implant can be designed to form one or more artificial facets on a vertebral body which can be used to improve a patient's spinal function. Many methodologies can be used with the spinal implant, depending in part on the configuration of the spinal implant. When the spinal implant is a clamped-shaped device that includes at least two arms or legs, the following non-limiting methodology can be used: 1) Exposure of a surgical site (e.g., Surgical exposure via Open or minimally-invasive surgery ("MIS") approach, Preparation of one or more surfaces of the vertebra for bio-ingrowth, Small laminotomy in superior lamina, Small laminotomy in lateral pars, etc.); 2) Determine proper size of spinal implant; 3) Engage medial lamina foot on first leg of spinal implant; 4) Engage lateral pars foot on second leg of spinal implant; 5) Close or tighten clamp on spinal implant that is positioned across pars; 6) Manipulate position of spinal implant for optimum fixation and position; 7) Review position of spinal implant by MIS, radiological review, etc.; 8) Final tightening of spinal implant with set-screw or lock nut or other methodology; 9) Insert second spinal implant, if necessary; and 10) Attach one or more components to spinal implant (e.g., modular head, third or fourth "long arm", "lamina plate", cross-link, longitudinal member (e.g., rod, plate, motion preservation device, etc.), etc.). The spinal implant can have a variety of benefits such as, but not limited to, 1) Eliminate the need for a hospital to carry a large inventory of lamina hooks, wires, screws, buttons, etc.; 2) Provide enhanced fixation to a vertebral body or multiple vertebral bodies-clamp design, cortical bone, etc.; 3) Allow for forced coupling of the construct, if desired, for enhanced purchase and better control for manipulating the vertebra body and motion segment (deformity surgery); 4) Allow for bio-ingrowth capability for permanent fixation to lamina biologically; 5) Allow for the attachment of growth rods for pediatric scoliosis; 6) Provides a method of addressing the disease of Osteoporosis; 7) Facilitate in motion preservation in the spine, as compared to alternative surgical methodologies; 8) Allows for revision surgery to be undertaken with greater ease than current devices; 9) Enables "lamina prosthesis" for repair or reconstruction surgery; 10) Allows for the treatment of Tumors, Infections, Revision surgery, Trauma, etc.; 11) Permits the creation of a permanent "docking" site that can be revisited by the surgeon or a subsequent surgeon, if necessary; 12) Permit the ability to control vertebral motion or manipulation (e.g., De-Rotation, 3-D contouring, etc.); 13)

Provide similar advantages to standard pedicle screw fixation; 14) Allow for Uni or bilateral control or fixation; 15) Allow for Single or Multi-level construct using "links"; 16) Provide a substitute for pedicle screws when pedicle screws usage is impractical (small, osteoporotic, or missing pedicle); 17) Replace the pedicle screw prosthesis implant; 18) Provide a complement to the pedicle screw prosthesis implant system; 19) Can be attached to or be used with pedicel screw instrumentation; and/or 20) Can be attached to or be used with artificial vertebral body implant (360) reconstruction. The spinal implant can be at least partially formed of a material that has been created or modified utilizing injection molding technology so as to customize the spinal implant. The spinal implant can be staged using a MIS approach for bio-ingrowth application, such as surgically inserting a sleeve into the site and, later, inserting this device into the fixed sleeve site. The spinal implant can be designed so that at least a portion of the spinal implant promotes and/or allows bio-ingrowth to at least provide a solid fixation point to the bone, thereby minimizing loosening, and/or stress shielding and maximizes load sharing. The spinal implant can be formed of a variety of materials (e.g., solid metal, polymer, ceramic, memory metal, HA, etc.). The spinal implant can be at least partially coated with osteobiologics (BMPs, bone marrow concentrate, fillers, and substitutes.

One non-limiting object of the present invention is the provision of a spinal implant that can be used be in the posterior aspect of the spinal column for spinal reconstruction, revision surgery, deformity correction, tumor, and trauma surgery of the cervical, thoracic, and/or lumbo-sacral spine.

Another and/or alternative non-limiting object of the present invention is the provision of a spinal implant that can removably or irremovably secure onto the posterior elements of one or more spinal vertebrae.

Still another and/or alternative non-limiting object of the present invention is the provision of a spinal implant that can be secured within the interval between the superior margin of the lamina of a vertebra and the lateral margin of the pars interarticularis portion of the vertebra.

Yet another and/or alternative non-limiting object of the present invention is the provision of a spinal implant that can span at least a portion of the length of the pars interarticularis, or span more than one vertebra's surface.

Still yet another and/or alternative non-limiting object of the present invention is the provision of a spinal implant that can provide strong permanent or temporary fixation to the posterior elements of a vertebra or multiple vertebrae.

A further and/or alternative non-limiting object of the present invention is the provision of a spinal implant that can allow for a variety of attachments to be placed upon and/or connected to the spinal implant.

Still a further and/or alternative non-limiting object of the present invention is the provision of a spinal implant that can simplify spinal procedures and/or facilitate the improvement of the patient's health.

Yet a further and/or alternative non-limiting object of the present invention is the provision of a spinal implant that can replace the need for lamina and transverse process hooks, pedicle screws, sub-laminar wires, and/or spinous process buttons.

Still yet a further and/or alternative non-limiting object of the present invention is the provision of a spinal implant that can eliminate the need for a hospital or other medical facility to carry a large inventory of lamina hooks, wires, screws, buttons, etc.

Another and/or alternative non-limiting object of the present invention is the provision of a spinal implant that can provide enhanced fixation to a vertebral body or multiple vertebral bodies.

Still another and/or alternative non-limiting object of the present invention is the provision of a spinal implant that can allow for bio-ingrowth capability for permanent fixation to lamina biologically.

Yet another and/or alternative non-limiting object of the present invention is the provision of a spinal implant that can allow for the attachment of growth rods for pediatric scoliosis.

Still yet another and/or alternative non-limiting object of the present invention is the provision of a spinal implant that can be used to treat the disease of Osteoporosis.

A further and/or alternative non-limiting object of the present invention is the provision of a spinal implant that can facilitate in motion preservation in the spine.

Still a further and/or alternative non-limiting object of the present invention is the provision of a spinal implant that can allow for revision surgery to be undertaken with greater ease.

Yet a further and/or alternative non-limiting object of the present invention is the provision of a spinal implant that can enable "lamina prosthesis" for repair or reconstruction surgery.

Still yet a further and/or alternative non-limiting object of the present invention is the provision of a spinal implant that can allow for the treatment of tumors, infections, revision surgery, and/or trauma to the spin or regions about the spine.

Another and/or alternative non-limiting object of the present invention is the provision of a spinal implant that can permit the creation of a permanent "docking" site for one or more components.

Still another and/or alternative non-limiting object of the present invention is the provision of a spinal implant that can permit the ability to control vertebral motion or manipulation.

Yet another and/or alternative non-limiting object of the present invention is the provision of a spinal implant that can provide similar advantages to standard pedicle screw fixation.

Still Yet another and/or alternative non-limiting object of the present invention is the provision of a spinal implant that can allow for unilateral or bilateral control or fixation.

A further and/or alternative non-limiting object of the present invention is the provision of a spinal implant that can allow for single or multi-level construct using "links".

Still a further and/or alternative non-limiting object of the present invention is the provision of a spinal implant that can provide a substitute for pedicle screws.

Yet a further and/or alternative non-limiting object of the present invention is the provision of a spinal implant that can provide a complement to the pedicle screw prosthesis implant system.

Still yet a further and/or alternative non-limiting object of the present invention is the provision of a spinal implant that can be attached to or be used with pedicel screw instrumentation.

Another and/or alternative non-limiting object of the present invention is the provision of a spinal implant that can be attached to or be used with artificial vertebral body implant reconstruction.

These and other advantages will become apparent to those skilled in the art upon the reading and following of this description taken together with the accompanying drawings.

BRIEF DESCRIPTION OF THE DRAWINGS

Reference may now be made to the drawing, which illustrates an embodiment that the invention may take in physical form wherein:

FIGS. 9A-9D, and 10-13 illustrate non-limiting alternative configurations of the arm adjustment mechanism of FIG. 1;

DETAILED DESCRIPTION OF THE INVENTION

Figure 1:
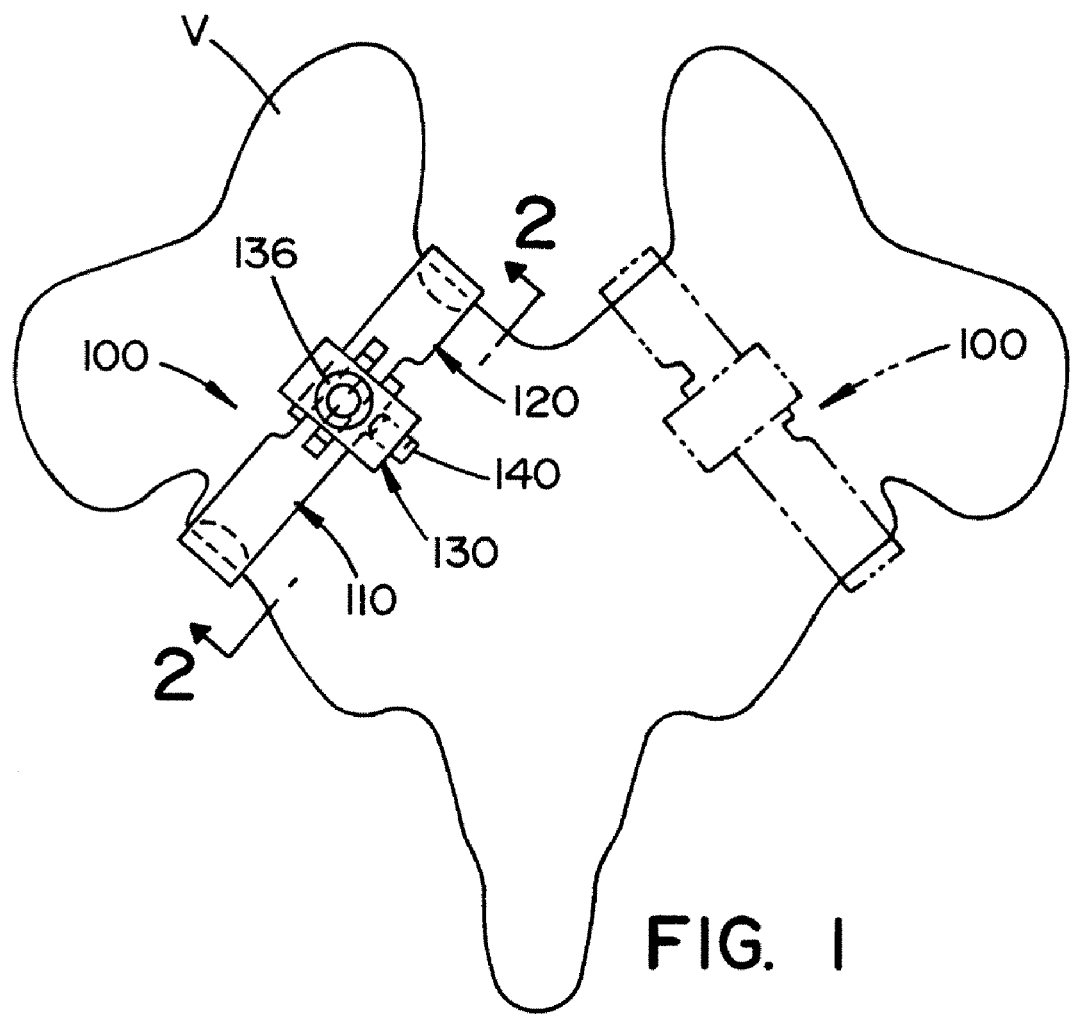
FIG. 1 is an elevation view of one non-limiting embodiment the spinal implant in accordance with the present invention connected to a vertebra.

Referring now to the preferred embodiment of the drawings, wherein the showings are for the purpose of illustrating a preferred embodiment of the invention only and not for the purpose of limiting the invention, FIGS. 1-15 illustrate a spinal implant 100 in accordance with the present invention. As best illustrated in FIG. 1, the spinal implant is designed to be at least partially secured to the posterior elements of a spinal vertebra V. In particular, the spinal implant, as shown in FIG. 1, is secured to the vertebra V within the interval between the superior margin of the lamina of the vertebra and the lateral margin of the pars interarticularis portion of the vertebra. As can be appreciated, the spinal implant can be designed to span the full length of the pars interarticularis, a portion of the pars interarticularis, or connect to more than one vertebra. As best illustrated in FIG. 1, one or more spinal implants 100 can be secured to a vertebra.

As illustrated in FIGS. 3-8, the spinal implant includes at least two arms 110, 120. At least one arm is designed to be adjustably connected to an arm hub 130. Each arm 110, 120 includes a body portion 112, 122 and an end foot 114, 124. The body portion of both arms is illustrated are being generally planar or flat; however, it can be appreciated that the body portion can be slightly curved and/or include other configurations. The end foot on the end of each arm is designed to secure the end portion of the arms to a portion of a vertebra. Each foot is angularly oriented with respect to the body portion of the arms; however, this is not required. Each foot is illustrated as having a maximum angular orientation of over 90° relative to the longitudinal axis of the body portion. Typically, the maximum angular orientation is about 90-160°, and more typically about 90-130°; however, other angles can be used. As can be appreciated, the maximum angular orientation can be less than 90°. The angular orientation of the feet can be the same or different. The inner surface of each foot has a generally planar or slightly curved profile; however, it can be appreciated that one or more of the feet can include other configurations.

Although not shown, the inner surface of one or more feet can include one or more structures and/or materials to facilitate in the gripping of the one or more feet of the arms to a portion of the vertebra; however, this is not required. For instance, one or more feet can include one or more gripping arrangements such as, but not limited to, one or more teeth, one or more ribs, one or more rough regions, etc.; however, this is not required. In addition or alternatively, an adhesive (e.g., bone cement, bio-grout, polymer adhesive, etc.) can be used to facilitate in the gripping of the one or more feet of the arms to a portion of the vertebra; however, this is not required. Furthermore, one or more portions of one or more feet can alternatively or additionally be porous and/or include one or more openings or cavities so as to promote bone ingrowth, and thereby facilitate in the gripping of the one or more feet of the arms to a portion of the vertebra; however, this is not required. The one or more porous regions can include one or more materials (e.g., bone, etc.), medication, drugs, etc. to promote and/or inhibit bone growth on one or more regions of the feet; however, this is not required. As can be appreciated, other or additional arrangements can be used to facilitate in the gripping and/or proper operation of the one or more feet of the arms on a portion of the vertebra.

As illustrated in FIGS. 3-8, the body section and foot of each arm is formed of a single piece of material. Typically, the material is a metal material; however, other or additional materials can be used. As can be appreciated, the body portion and the foot of one or more arms can be formed of different materials. The body portion and foot of each arm is also illustrated as being about the same shape and size. As can be appreciated, the body portion and/or foot of each arm can be the same or different from another arm. For instance, the length, profile, thickness and/or cross-sectional shape of the body portion of each arm can be the same or different of the body portion of one or more other arms. Furthermore, the length, profile, thickness and/or cross-sectional shape of the foot of each arm can be the same or different from the foot of one or more other arms. Although not shown, the foot on one or more arms can be designed so as to be connected to the body portion by use of an adhesive, solder, weld, etc.; however, this is not required. As can further be appreciated, the foot can be designed so as to be adjustably oriented relative to the body portion by use of a hinge mechanism, a ratchet mechanism, ball/socket mechanism, etc.; however, this is not required. A set screw and/or other locking arrangement can be used to adjust and/or secure the adjustable foot in place; however, this is not required.

Figure 3:
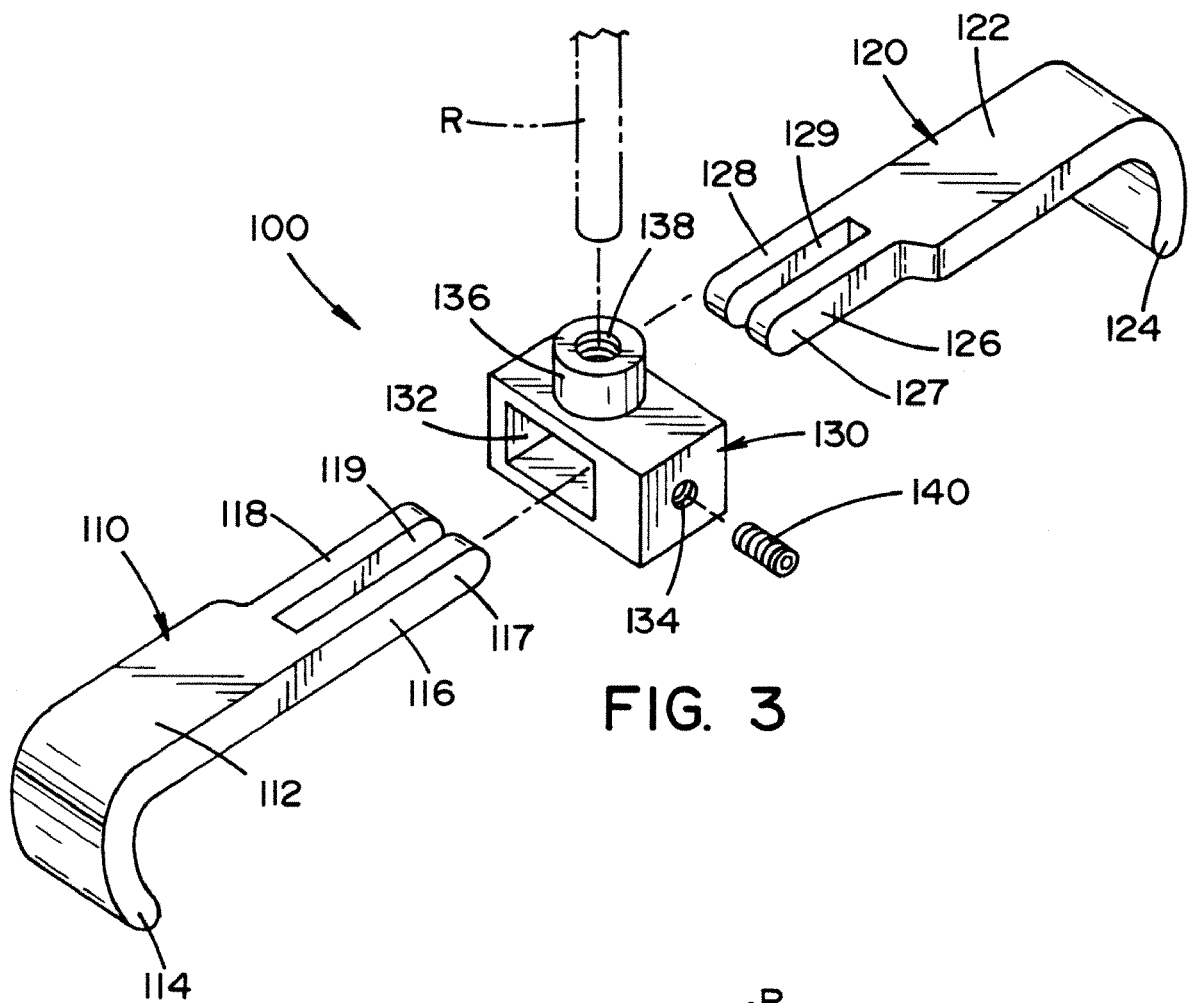
FIG. 3 is an exploded view of the spinal implant of FIG. 1.
Figure 4:
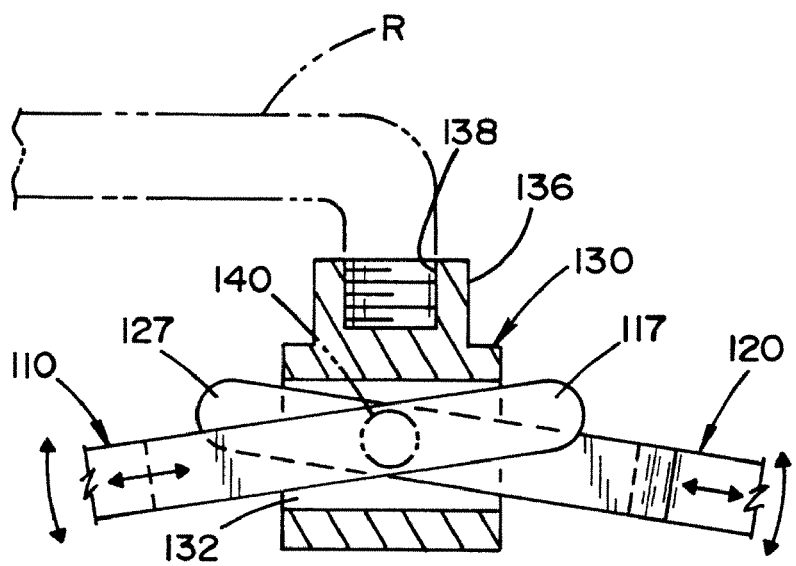
FIG. 4 is an enlarged sectional view of the arm adjustment mechanism for two arms of the spinal implant of FIG. 1.
Figure 5:
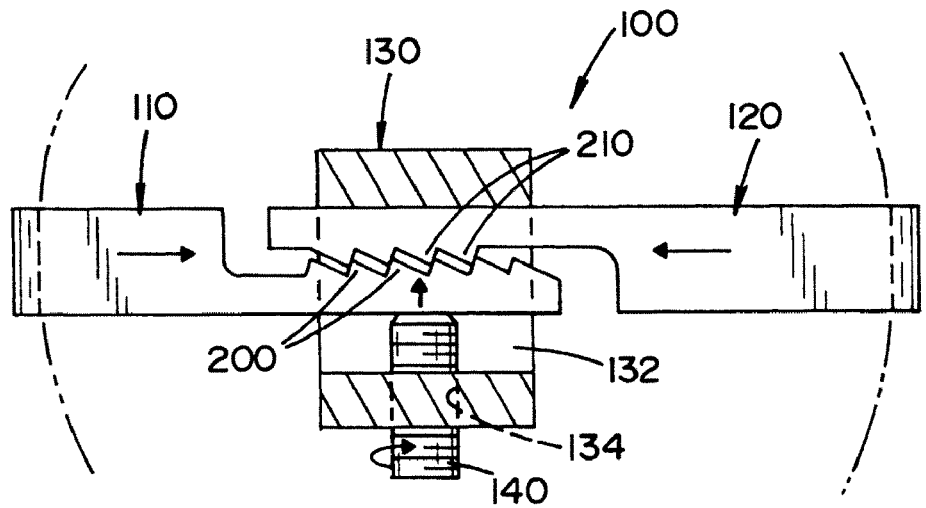
FIG. 5 is an enlarged sectional view of a non-limiting alternative arm adjustment mechanism for two arms of the spinal implant.
Figure 6:
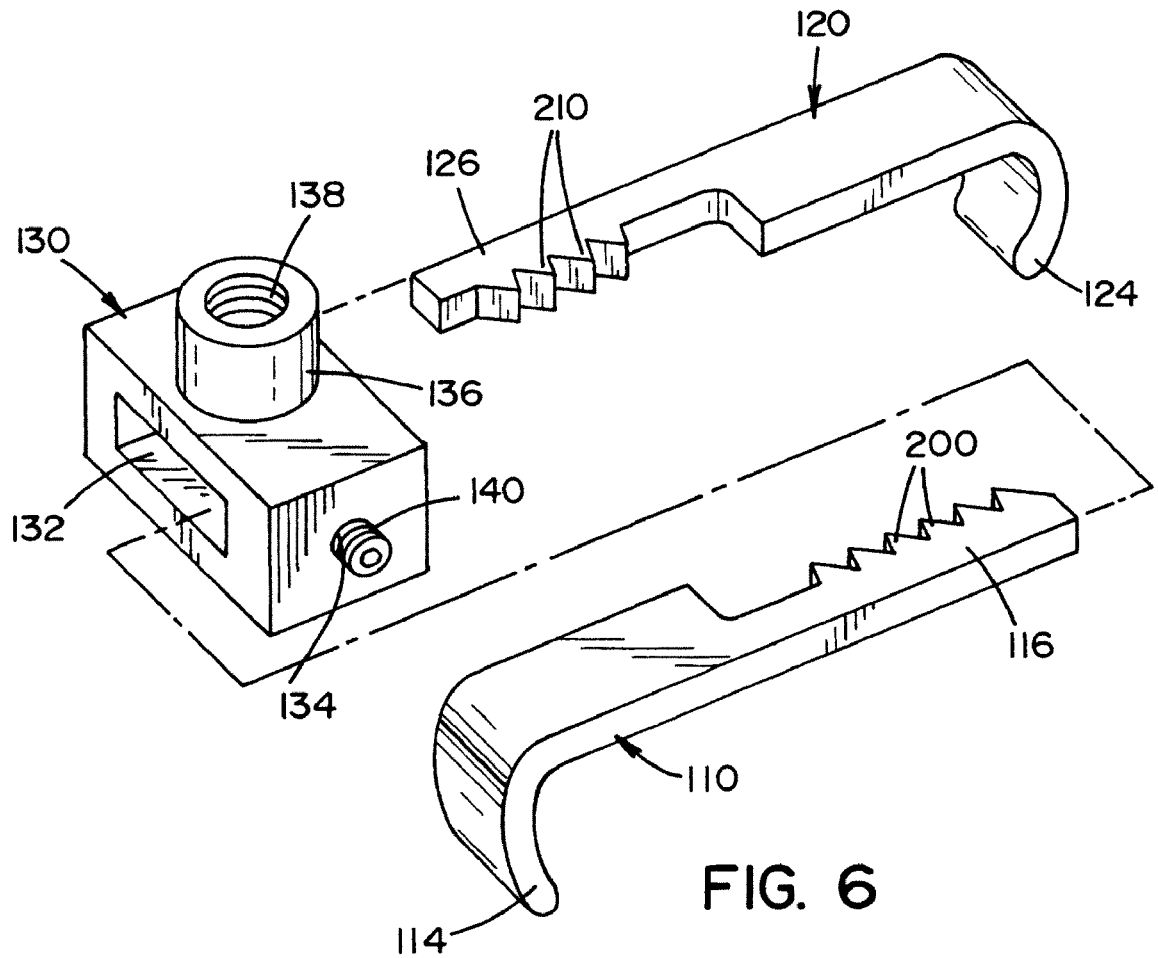
FIG. 6 is an exploded view of the spinal implant that includes the arm adjustment mechanism of FIG. 5.
Figure 7:
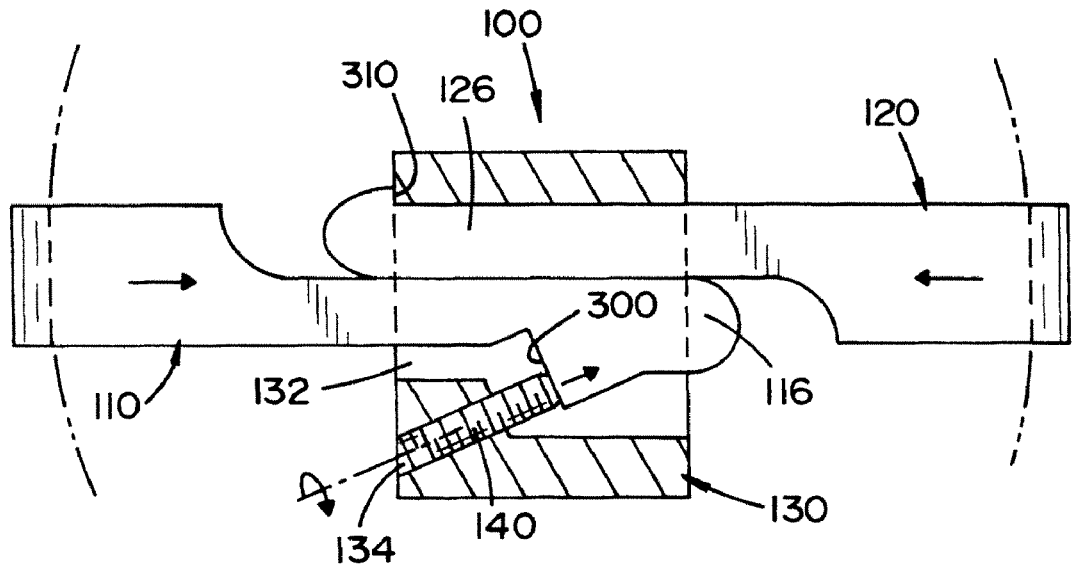
FIG. 7 is an enlarged sectional view of a non-limiting alternative arm adjustment mechanism for two arms of the spinal implant.
Figure 8:
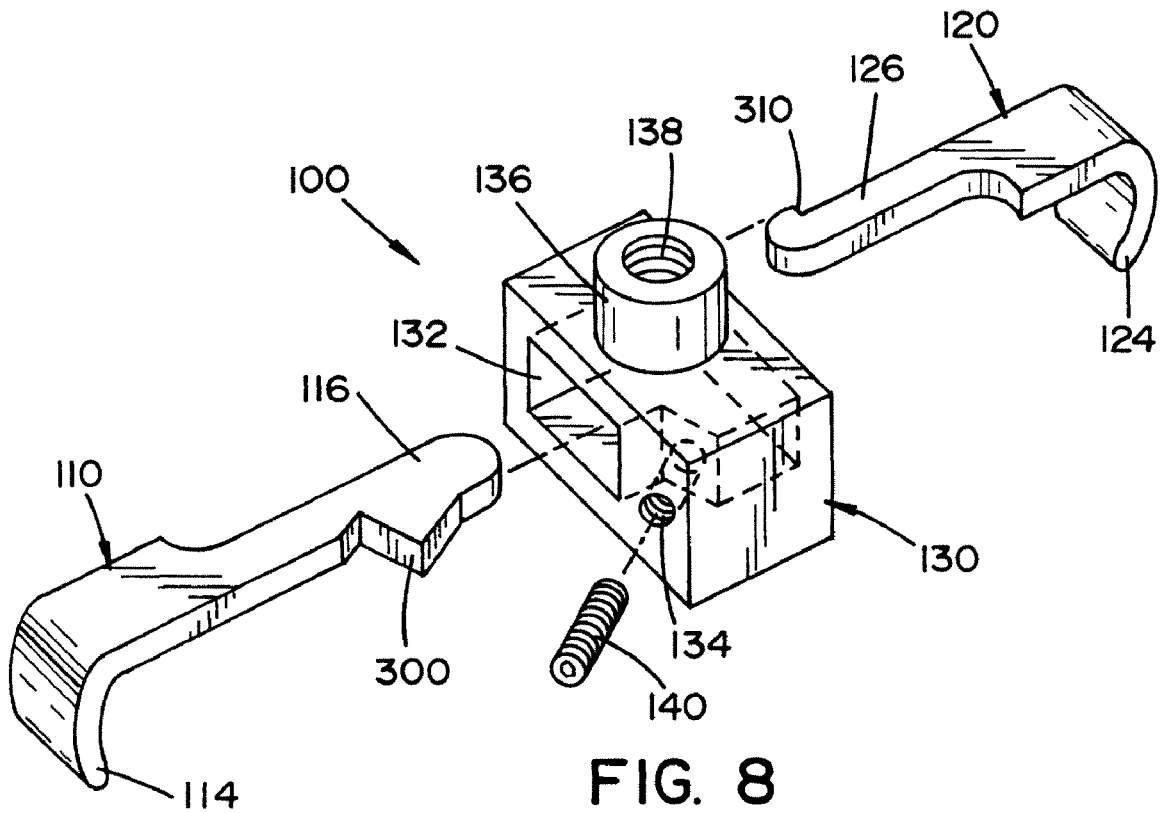
FIG. 8 is an exploded view of the spinal implant that includes the arm adjustment mechanism of FIG. 7.

The orientation of the two arms relative to one another can be accomplished in a variety of ways. As can be appreciated, the spinal implant can include more than two arms; however, this is not required. The arrangement used to orient the arms can be designed to orient the arms about one or more axes of the spinal implant. A first non-limiting arrangement is illustrated in FIGS. 3 and 4, a second non-limiting arrangement is illustrated in FIGS. 5 and 6, and a third non-limiting arrangement is illustrated in FIGS. 7 and 8. In all the examples illustrated in FIGS. 3-8, the spinal implant includes two arms that are adjustable along the longitudinal length of the spinal implant. As can be appreciated, these three arrangements merely illustrate a few of the possible arrangements that can be used to orient and set in position the arms relative to one another. As can be appreciated, the spinal implant can be designed such that one or more of the arms are not adjustable along the longitudinal axis of the spinal implant; however, this is not required. As can also be appreciated, one or more arms can be adjustably oriented in one or more less axes that one or more other arms; however, this is not required. For instance, one or more arms could be adjustably oriented in one or more axes of the spinal implant, and one or more arms could be adjustably oriented in no axis of the spinal implant. In another instance, one or more arms could be adjustably oriented in two or more axes of the spinal implant, and one or more arms could be adjustably oriented in only one axis of the spinal implant. In still another instance, one or more arms could be adjustably oriented in three axes of the spinal implant, and one or more arms could be adjustably oriented in two or one axes of the spinal implant.

Referring again to FIGS. 3 and 4, arm hub 130 includes an arm opening 132 that enables front portions 116, 126 of arms 110, 120 to be at least partially telescopically received in the arm opening. Each of the front portions of the arms include two legs 117, 118, 127, 128 that are separated by a slot 119, 129. The configuration of the front portions of the two arms is such that when both front portions of the arms are partially inserted into opening 132, leg 118 of arm 110 partially enters slot 129 of arm 120 and leg 127 of arm 120 partially enters slot 119 of arm 110. This engagement of the front portion of the arms in the arm hub is partially illustrated in FIG. 4. As illustrated by the arrows in FIG. 4, the two arms of the spinal implant are both adjustable along the longitudinal and latitudinal (i.e., 90° to a longitudinal axis) axes of the spinal implant. Once the arms are positioned on a portion of one or more vertebra, the arms can be set relative to one another by use of a set screw 140. Set screw 140 is a threaded screw that is designed to be inserted into set opening 134 of arm hub 130. The set opening is positioned on one side of the arm hub; however, it can be appreciated that the set opening can be position in other locations on the arm hub (e.g., bottom side, top side, front end, back end, etc.). It can also be appreciated that more than one set opening can be used to set the anus in position in the arm hub. The set opening includes a thread to receive the thread on set screw 140. The head of the set screw includes a configuration that enables a tool to engage the top of the set screw so as to insert/remove the set screw from the set opening. When the set screw is inserted into the set opening, the front end of the set screw engages a side portion of leg 116 and causes the arm 110 to move into arm 120, which in turn causes leg 128 to engage an inner side surface of opening 132. The pressure exerted on arm 110 by the set screw causes the two arms to be set in position in arm hub 130. Removal of the set screw from the set opening can enable the arms to be adjusted in the arm opening. As can be appreciated, arrangements other than the set screw can be used to set the arms relative to one another (e.g., set pin, adhesive, adhesive, clamp arrangement, etc.).

Arm hub 130 also includes one or more connection arrangements 136. As illustrated in FIGS. 3 and 4, the connection arrangement 136 is positioned on the top surface of the arm hub. As can be appreciated, the connection arrangement 136 can be located on other regions of the arm hub. As also can be appreciated, the arm hub can include more than one connection arrangement. The one or more connection arrangements on the arm hub are designed to connection to a stabilizing system and/or other type of treatment system (e.g., modular heads; one or more attachment sites for rods, plates, and/or medication delivery devices, etc.), and/or connect another arm to the spinal implant. Connection arrangement 136, as illustrated in FIGS. 3 and 4, includes a threaded cavity 138 designed to receive a threaded end of a stabilizing system and/or other type of treatment system such as, but not limited to, a threaded end of a rod R. As can be appreciated, the connection arrangement 136 can have many other and/or additional configurations (e.g., slot configuration, ball configuration, polyaxial head, etc.) so as to connect a variety of stabilizing systems and/or other type of treatment system to the spinal implant. Although not shown, the connection arrangement 136 can be designed to be removable so that other types of connection arrangements can be connected to the arm hub to enable other types of stabilizing systems and/or other type of treatment system to be connected to the spinal implant; however, this is not required. The connection arrangement 136 is illustrated as extending outwardly from a surface of the arm hub; however, this is not required. As can be appreciated, the connection arrangement can be formed at least partially internally in the arm hub such that little, if any, portion of the connection arrangement extends outwardly from the surface of the arm hub.

Referring now to FIGS. 5 and 6, a different configuration of arms 110 and 120 is shown. The front portion of each of the arms includes a plurality of teeth 200, 210. The teeth are designed to engage one other when a portion of each arm is positioned in the arm opening 132 of arm hub 130 and the set screw 140 is inserted into set opening 134 as illustrated in FIG. 5. The teeth configuration of the arms can be designed to create a ratcheting configuration for the arms when positioning the arms relative to one another; however, this is not required. As the set screw 140 is inserted into set opening 134 as illustrated by the arrow in FIG. 5, the front end of the screw engages the side of arm 110 and moves the arm into engagement with arm 120, which in turn causes arm 120 to engage an inner wall of opening 132. The pressure exerted by the set screw causes the two arms to be set in opening 132 of arm hub 130. The removal of the set screw enables arms 110, 120 to be adjustable positioned in arm hub 130. As can be appreciated, the location of opening 132 can be in other locations as described above with regard to FIGS. 3 and 4. As can be appreciated, other or additional mechanisms can be used to adjust/set one or more of the arms in arm hub 130 as described above with regard to FIGS. 3 and 4. The design of arms 110, 120 in FIGS. 5 and 6 enables the arms to be adjusted along the longitudinal axis of the spinal implant as illustrated by the arrows in FIG. 5. Due to the configuration of the teeth on the arms, the arms are primarily adjustable on the longitudinal axis of the spinal implant; however, the teeth could be designed to enable one or both arms to be adjustable in an axis other than the longitudinal axis. A connection arrangement 136 having a threaded cavity 138 is positioned on the top surface of the arm hub. The connection arrangement is designed to connection to a stabilizing system and/or other type of treatment system, and/or connect another arm to the spinal implant. A variety of designs, orientations and number of connection arrangement can be used as described above with regard to FIGS. 3 and 4.

Referring now to FIGS. 7 and 8, a different configuration of the arms and arm hub is illustrated. Arm 110 includes a front portion 116 that includes an adjustment landing 300. Arm 120 includes a front portion 126 that includes a stop landing 310. As illustrated in FIG. 7, a portion of the front portions of both arms are designed to be insertable in arm opening 132 of arm hub 130. Stop landing 310 limits the movement of arm 120 in one direction along the longitudinal axis of the spinal implant as shown in FIG. 7. Adjustment landing 300 on arm 110 is used to adjust the longitudinal position of arm 110. An adjustment screw 140 is designed to be threaded into set opening 134 of arm hub 130. As shown in FIG. 7, as the adjustment screw is threaded into set opening 134, the front end of the set screw engages adjustment landing 300, thereby pushing the front portion of arm 110 into the front portion of arm 120 to cause both arms to be set in arm hub 130. As shown in FIG. 7, the arms are adjustable along the longitudinal axis of the spinal implant as illustrated by the arrows. This particular arm configuration can allow the one or both arms to be adjustable in an axis other than the longitudinal axis. As can be appreciated, the location of opening 132 can be in other locations on arm hub 130 as described above with regard to FIGS. 3 and 4. As also can be appreciated, other or additional mechanisms can be used to adjust/set one or more of the arms in arm hub 130 as described above with regard to FIGS. 3 and 4. A connection arrangement 136 having a threaded cavity 138 is positioned on the top surface of the arm hub. The connection arrangement is designed to connection to a stabilizing system and/or other type of treatment system, and/or connect another arm to the spinal implant. A variety of designs, orientations and number of connection arrangement can be used as described above with regard to FIGS. 3 and 4.

The three non-limiting configurations of the spinal implant illustrated in FIGS. 3-8, merely set forth three of a number of arrangements that can be used to adjustably position the one or more arms of the spinal implant relative to one another. Other non-limiting arrangements can include, but are not limited to, 1) one or more arms connected to the arm hub by a hinge, 2) one or more arms connected to the arm hub by a ball and socket arrangement, 3) one or more arms connected to the arm hub by a slot arrangement, 3) one or more arms secured to the arm hub by a threaded connection, etc. As illustrated in FIGS. 3-8, both arms of the spinal implant are adjustable in at least one axis of the spinal implant; however, it can be appreciated that one or more of the arms of the spinal implant are in a fixed positioned relative to the arm hub; however, this is not required.

Referring now to FIGS. 9A-D and 10-13, there are illustrated a variety of arm hub configurations that could be used to connect to a variety of components of a stabilizing system and/or other type of treatment system. As can be appreciated, the various configurations of the arm hubs shown in FIGS. 9A-D and 10-13 are non-limiting examples of just a few of the many arm hub configurations that can be used in conjunctions with the spinal implant of the present invention.

Referring now to FIG. 9A, there is illustrated an arm hub 130 having a similar configuration as the arm hub of FIGS. 3 and 4 except that the connection arrangement 400 is in the shape of a polyaxial head. As can be appreciated, the polyaxial head can be used on other arm hubs such as, but not limited to, the arm hubs illustrated in FIGS. 5-8.

Referring now to FIG. 9B, there is illustrated an arm hub 130 having a similar configuration as the arm hub of FIGS. 3 and 4 except that the connection arrangement 500 is in the shape of a ball. As can be appreciated, the ball-shaped connection arrangement can be used on other arm hubs such as, but not limited to, the arm hubs illustrated in FIGS. 5-8.

Figure 9C:
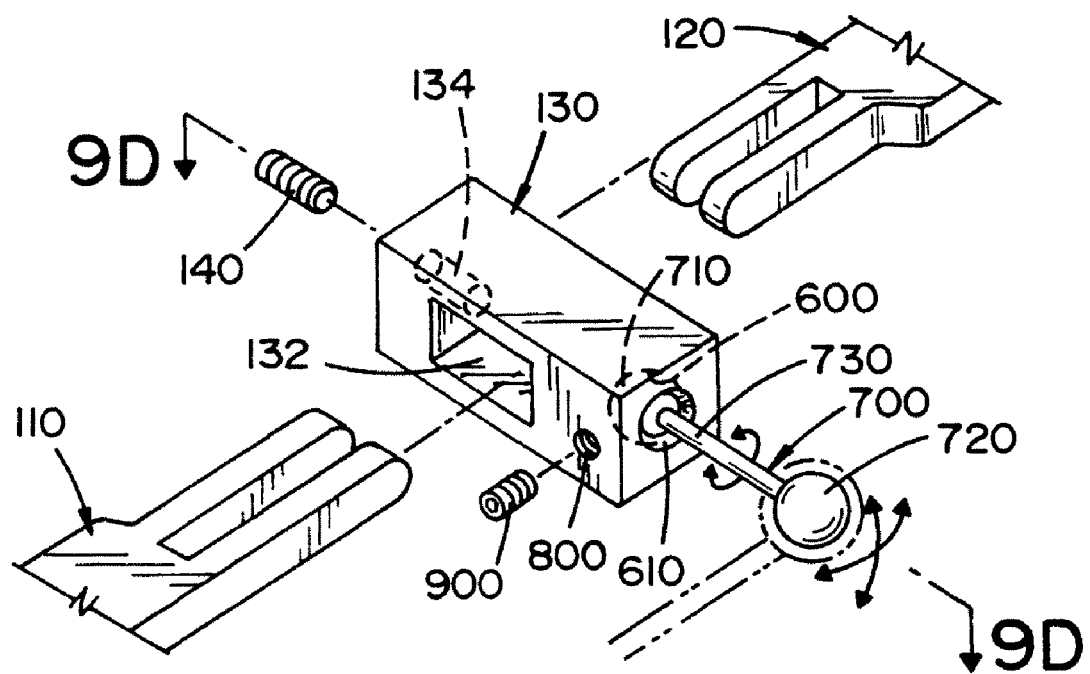
Figure 9D:
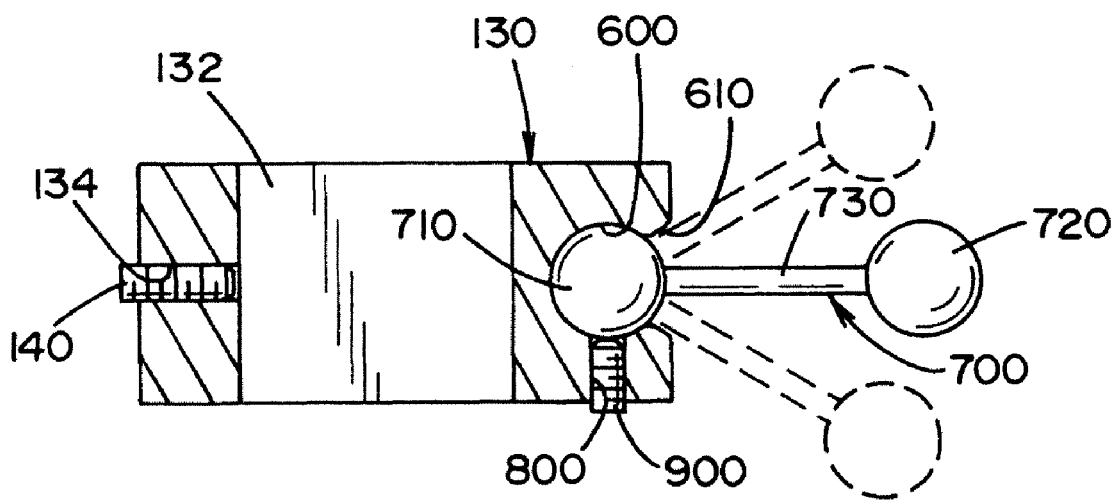

Referring now to FIGS. 9C and 9D, there is illustrated a modified version of the arm hub shown in FIGS. 3 and 4. The arm hub is absent a connection arrangement 136 on the top surface of the arm hub; however, it can be appreciated that a connection arrangement similar to connection arrangements 136, 400, 500 as discussed above could also be included on the arm hub. The connection arrangement on the side of arm hub 130 shown in FIGS. 9C and 9 D is in the form of a partially spherical cavity 600. The cavity 600 is accessed from the side of the arm hub by a tapered opening 610. As can be appreciated, cavity 600 can be located in other or additional regions of the arm hub. Cavity 600 is designed to receive a universal connector device 700 that includes a two generally spherical shaped ends 710, 720 which are connected by a rod-shaped member 730. As can be appreciated, end 720 have a variety of other shapes to enable end 720 to connect with and/or interact with a variety of stabilizing systems and/or other type of treatment systems. End 710 is designed to be at least partially positioned in cavity 600. The shape of cavity 600 and end 710 enables connector device 700 to be moved in a variety of positioned as indicated by the arrows in FIGS. 9C and 9D. The ability to move the connector device 700 in a variety of positions enhances the versatility of the spinal implant so that the spinal implant can be used with a variety of stabilizing systems and/or other type of treatment systems. The arm hub also includes a set opening 800 that is designed to receive a set screw 900. As shown in FIG. 9D, as the set screw is threaded into set opening 800, the front end of the set screw enters cavity 600 and engages end 710 of connection device 700, thereby pushing the end into the side of cavity 600 to cause end 710 to be substantially immovably positioned in cavity 600. The head of the set screw is typically designed to allow an instrument to insert/remove the set screw in/from opening 800; however, this is not required. The loosening of the set screw 900 enables connector device 700 to again be adjusted, if so desired. As can be appreciated, the location of opening 800 can be in other locations on arm hub 130. As also can be appreciated, other or additional mechanisms can be used to adjust/set end 710 in cavity 600.

Referring now to FIG. 10, there is illustrated another modified version of the arm hub shown in FIGS. 3 and 4. The arm hub is absent a connection arrangement 136 on the top surface of the arm hub; however, it can be appreciated that a connection arrangement similar to connection arrangements 136, 400, 500 as discussed above could also be included on the arm hub. The connection arrangement on the side of arm hub that is shown in FIG. 10 is in the form of tubular slot 1000. The tubular slot is illustrated as being positioned fully through the side of the arm hub; however, this is not required. As can be appreciated, the tubular slot can have other or additional cross-sectional shapes along the length of the slot (e.g., oval, polygonal, etc.). As can be appreciated, slot 1000 can be located in other or additional regions of the arm hub. Slot 1000 is designed to receive one or more components R of a stabilizing system and/or other type of treatment system (e.g., rod, etc.). As illustrated by the arrows, component R can be adjusted along the length of the slot. The tubular shape of slot 1000 in conjunction with the tubular shape of the end of component R enables component R to be rotated in the slot as indicated by the arrows; however, this is not required. The ability to move component R in a variety of positions enhances the versatility of the spinal implant so that the spinal implant can be used with a variety of stabilizing systems and/or other type of treatment systems. The arm hub also includes a set opening 1100 that is designed to receive a set screw 1200. As the set screw is threaded into set opening 1100, the front end of the set screw enters slot 1000 and engages a portion of component R that is positioned in slot 1000, thereby pushing a portion of component R into the side of slot 1000 and causing component R to be substantially immovably positioned in slot 1000. The head of the set screw is typically designed to allow an instrument to insert/remove the set screw in/from opening 1100; however, this is not required. The loosening of the set screw 1200 enables component R to again be adjusted, if so desired. As can be appreciated, the location of opening 1100 can be in other locations on arm hub 130. As also can be appreciated, other or additional mechanisms can be used to adjust/set component R in slot 1000.

Figure 11:
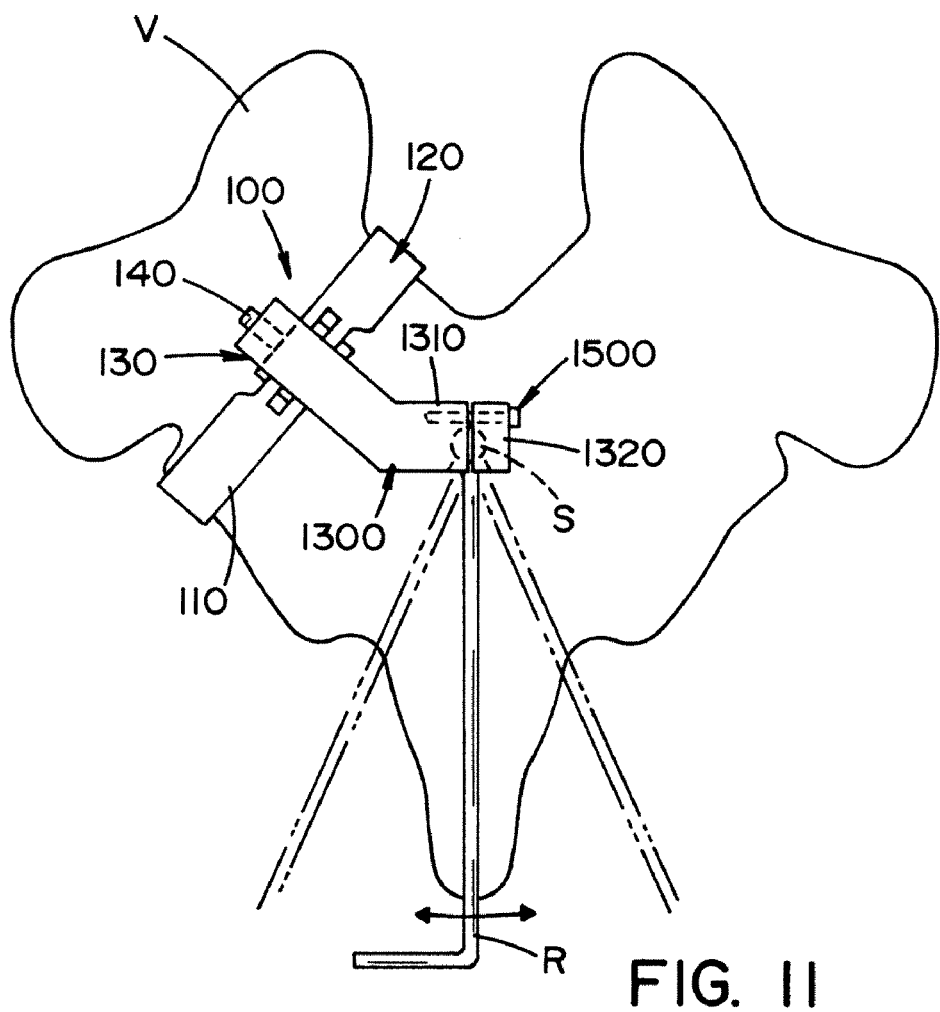
Figure 12:
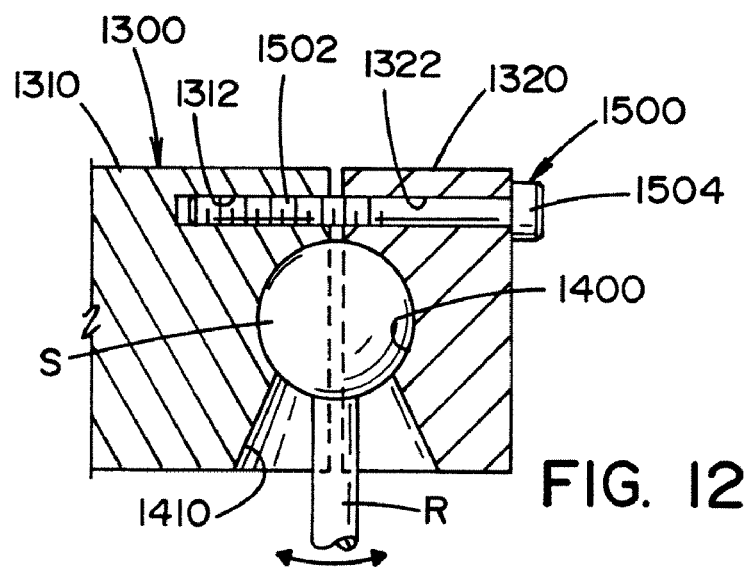
Figure 13:
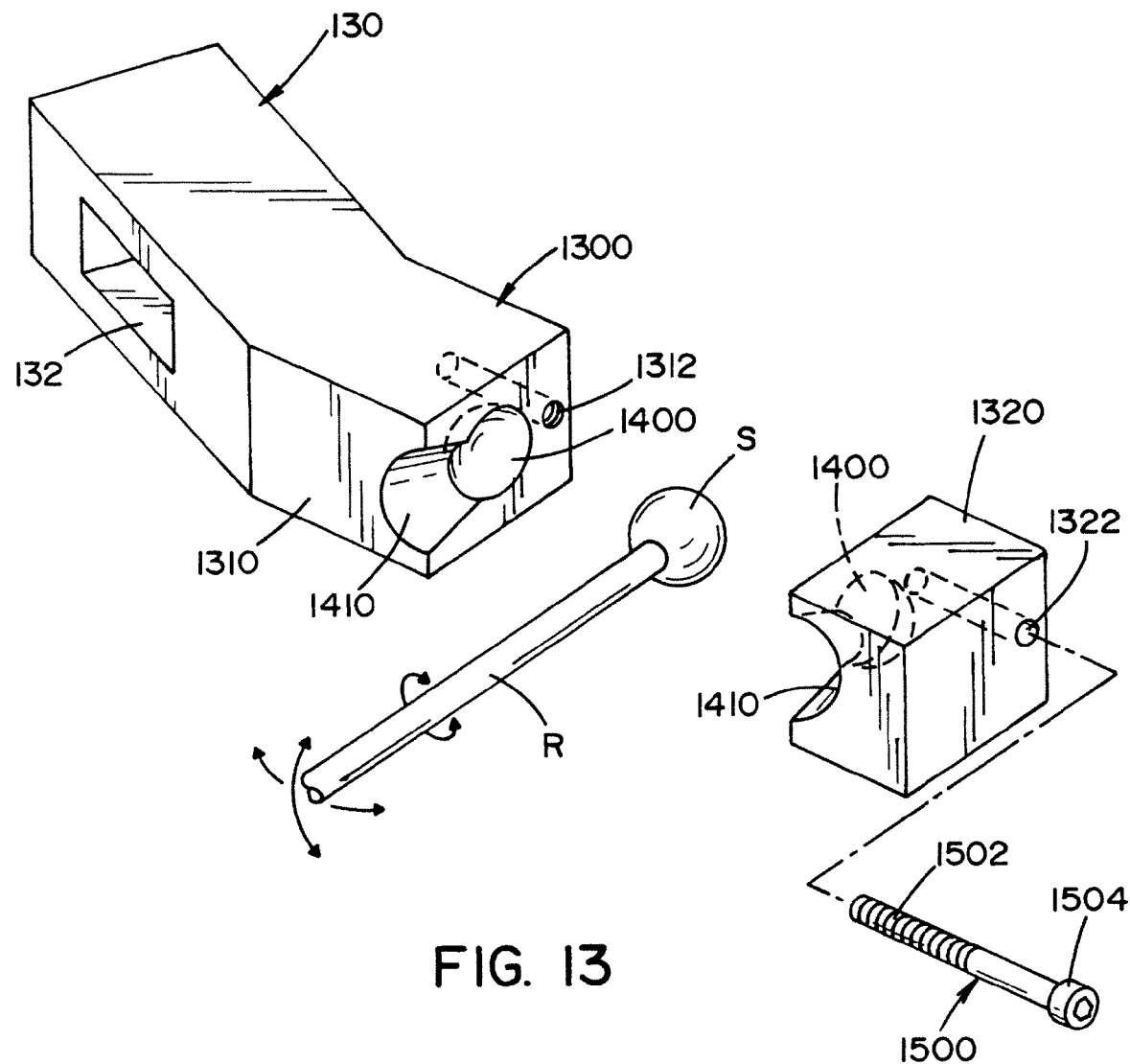

Referring now to FIGS. 11-13, there is illustrated another modified version of the arm hub shown in FIGS. 3 and 4. The arm hub is absent a connection arrangement 136 on the top surface of the arm hub; however, it can be appreciated that a connection arrangement similar to connection arrangements 136, 400, 500 as discussed above could also be included on the arm hub. The connection arrangement on the side of arm hub that is shown in FIGS. 11 and 13 is in the form of an angulated extension member 1300 that includes a connection arrangement on a side of the extension member that is in the form of a partially spherical cavity 1400. The cavity 1400 is accessed from the side of the extension member by a tapered opening 1410. As can be appreciated, cavity 1400 can be located in other or additional regions of the extension member. Cavity 1400 is designed to receive designed to receive one or more components R of a stabilizing system and/or other type of treatment system (e.g., rod, etc.). As best shown in FIG. 13, component R includes a generally spherical shaped end S. End S is designed to be at least partially positioned in cavity 1400. The shape of cavity 1400 and end S enables component R to be moved in a variety of positions as indicated by the arrows in FIGS. 11-13. The ability to move component R in a variety of positions enhances the versatility of the spinal implant so that the spinal implant can be used with a variety of stabilizing systems and/or other type of treatment systems. As illustrated in FIG. 13, the extension member includes two section 1310, 1320. Section 1310 is secured to the main body of arm hub 130. Section 1310 is typically formed as a single piece with the main body of the arm hub and/or with the same material as the main body of arm hub 130 as shown in FIG. 13; however, this is not required. The angular orientation of section 1310 is typically about 5-90°; however, other angles can be used. As shown in FIG. 13, the top surfaces of section 1310 and the main body of arm hub 130 lie generally in the same plane; however, this is not required. The front end of section 1310 forms about 50% of cavity 1400; however, it can be appreciated that the front end of section 1310 can be formed so as to accept more or less or no portion of cavity 1400. A front side end portion of section 1310 forms about 50% of tapered opening 1410; however, it can be appreciated that the front side end of section 1310 can be formed so as to accept more or less or no portion of tapered opening 1410. Section 1320 is illustrated as being separate and detachable from section 1310; however, this is not required. One side of section 1320 forms about 50% of cavity 1400; however, it can be appreciated that the side of section 1320 can be formed so as to accept more or less or no portion of cavity 1400. A back side end portion of section 1320 forms about 50% of tapered opening 1410; however, it can be appreciated that the back side end of section 1320 can be formed so as to accept more or less or no portion of tapered opening 1410. As can also be appreciated, the tapered opening can be formed in other or additional regions of the extension member 1300. Section 1320 includes a connection passageway 1322 that is designed to receive a portion of a set screw 1500. The body 1502 of the set screw is sized and shaped to pass into and through at least a portion of connection passageway 1322. The head 1504 of the set screw has a size and/or shape that prevents the head from fully passing through connection passageway 1322. As can be appreciated, a portion of connection passageway 1322 can include a recess, not shown that is designed to receive a portion of head 1504; however, this is not required. The front end face of section 1310 also includes a connection passageway 1312 that is designed to receive a portion of body 1502 of set screw 1500. Connection passageway 1312 can include a thread that is designed to receive a thread on the body of set screw 1500; however, it can be appreciated that many connection arrangements can be used to secure sections 1310 and 1320 together by set screw 1500 and/or by one or more other or additional connection arrangements (e.g., adhesive, pin, latch, etc.). In the arrangement shown in FIGS. 11-13, the spherical end S of component R is inserted into cavity 1400 by loosening set screw 1500 so as to enable section 1310 and 1320 to be at least partially separated from one another. Once end S is positioned in cavity 1440, component R is secured in positioned by tightening the set screw 1500, The tightening of the set screw draws sections 1310 and 1320 together. The head of the set screw is typically designed to allow an instrument to insert/remove the set screw; however, this is not required. The loosening of the set screw 1500 enables component R to be again adjusted, if so desired. As can be appreciated, the location of passageways 1312, 1322 can be in other locations. As also can be appreciated, other or additional mechanisms can be used to adjust/set component R in cavity 1400.

Figure 2:
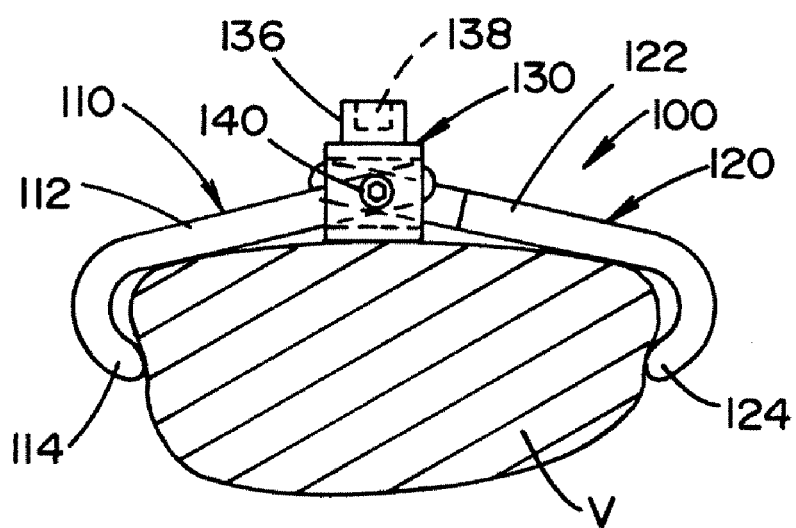
FIG. 2 is a cross-sectional view along line 2-2 of FIG. 1.

One non-limiting methodology for inserting spinal implant 100 on vertebra V as illustrated in FIGS. 1 and 2 is set forth; however, it will be appreciated that the spinal implant can be inserted on vertebra V in a different manner. Prior to inserting the spinal implant on a vertebra, an exposure procedure is performed to provide access to one or more vertebra, During this exposure procedure, one or more vertebra and/or a region about one or more vertebra may be prepared, treated, etc. prior to the insertion of the spinal implant. Prior to being the insertion process of the spinal implant, the proper size of the spinal implant is assessed. This assessment can take place prior to, during and/or after the exposure procedure. Once the proper spinal implant has been selected, one foot 114, 124 is inserted onto a portion of the vertebra. Typically, the first foot is positioned to engage the medial lamina of the vertebra. The foot can be adhesively secured to the vertebra, if desired. After the first foot is positioned on the vertebra, the second foot is then positioned on the vertebra such as, but not limited to, the lateral pars of the vertebra. This other foot can also or alternatively be adhesively secured to the vertebra, if desired. If the spinal implant includes more than two arm and feet, these additional feet can be positioned on the vertebra or a different vertebra. Once two or more feet of the spinal implant are positioned on Vertebra V, set screw 140 is tightened in opening 134 to secure arms 110, 120 in position relative to one another and relative to arm hub 130. The position of the spinal implant on the vertebra can be reviewed to determine if the spinal implant is properly positioned on the vertebra. If the spinal implant needs to be adjusted on the vertebra, the set screw can be loosened and retightened until the spinal implant is properly positioned on the vertebra. Once the spinal implant is properly positioned on the vertebra a component R such as, but not limited to, a rod that fully forms or forms a portion of a stabilizing system and/or other type of treatment system is positioned in opening 138 of connection arrangement 136. As set forth above, the spinal implant of the present invention can be used to secure one or more components of a stabilizing system and/or other type of treatment system to one or more vertebra with having to penetrate or substantially penetrate into the vertebra. As is appreciated, the spinal implant has many other or additional features and advantages as previously discussed above.

Figure 14:
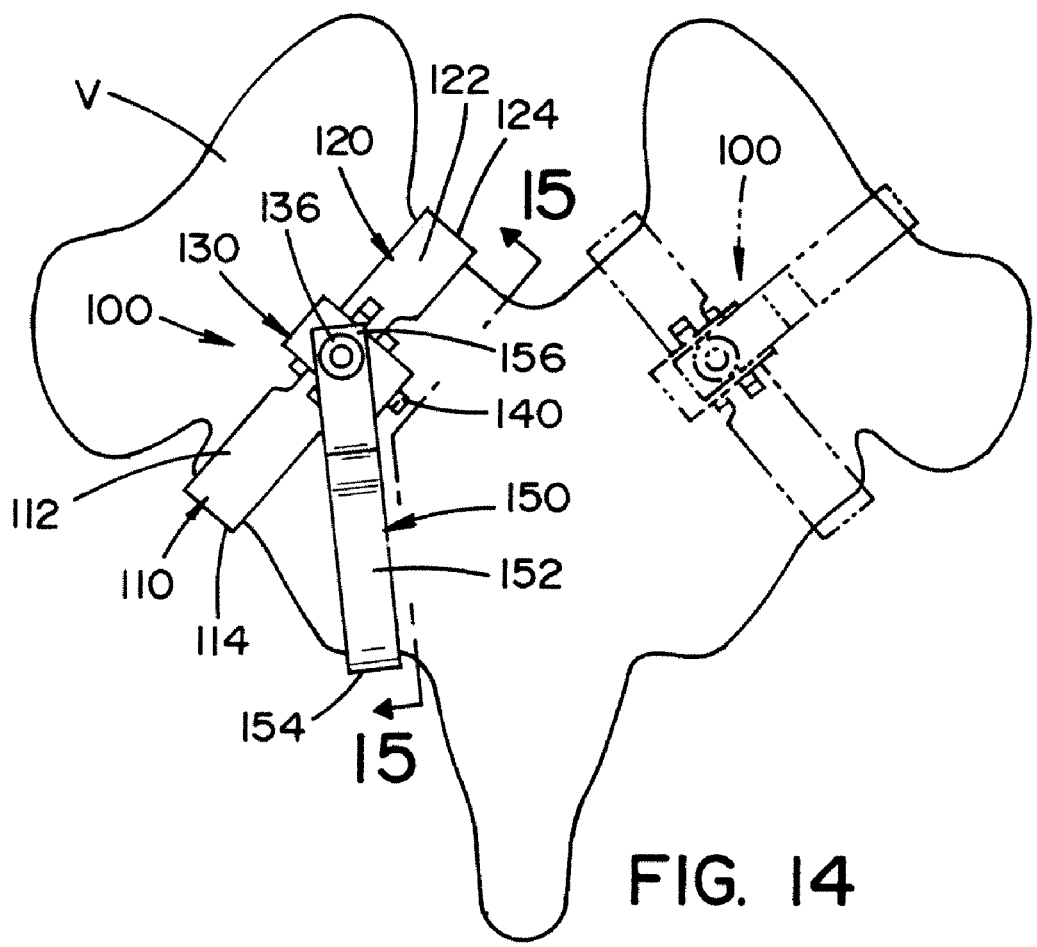
FIG. 14 is an elevation view of another non-limiting embodiment the spinal implant in accordance with the present invention; and, FIG. 15 is a cross-sectional view along line 15-15 of FIG. 14.
Figure 15:
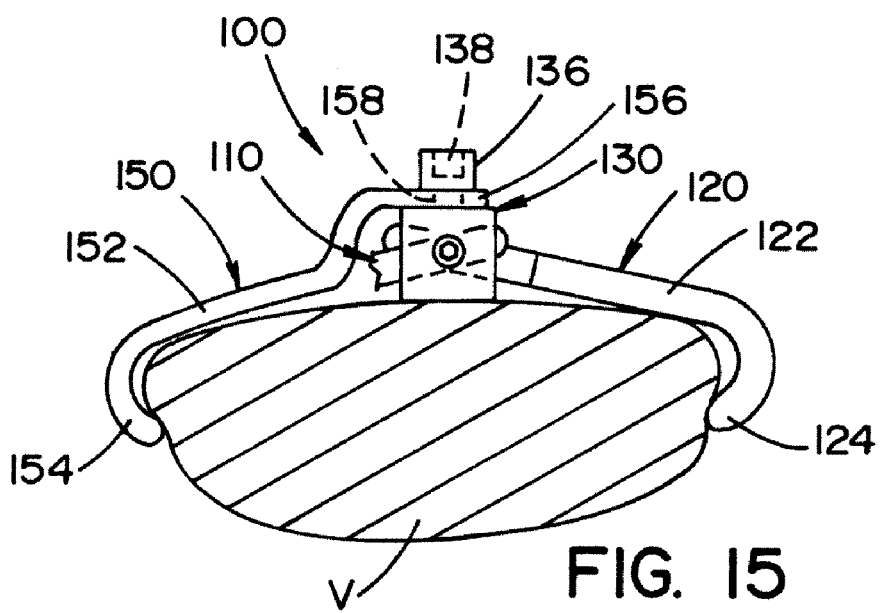

Referring now to FIGS. 14 and 15, there is illustrated a modified spinal implant 100 that includes three arms. The structure of the spinal implant is similar to the structure of the spinal implant described in FIGS. 1-13. The spinal implant illustrated in FIG. 14 includes two arms 110, 120 and a third arm 150. At least one arm is designed to be adjustably connected to an arm hub 130. Each arm 110, 120, 150 includes a body portion 112, 122, 152 and an end foot 114, 124, 154. The body portion of the arms is illustrated are being generally planar or flat; however, it can be appreciated that the body portion can be slightly curved and/or include other configurations. The end foot on the end of each arm is designed to secure the end portion of the arms to a portion of a vertebra. Each foot is angularly oriented with respect to the body portion of the arms; however, this is not required. Each foot is illustrated as having a maximum angular orientation of over 90° relative to the longitudinal axis of the body portion. Typically, the maximum angular orientation is about 90-160°, and more typically about 90-130°; however, other angles can be used. As can be appreciated, the maximum angular orientation can be less than 90°. The angular orientation of the feet can be the same or different. The inner surface of each foot has a generally planar or slightly curved profile; however, it can be appreciated that one or more of the feet can include other configurations.

Although not shown, the inner surface of one or more feet can include one or more structures and/or materials to facilitate in the gripping of the one or more feet of the arms to a portion of the vertebra; however, this is not required. For instance, one or more feet can include one or more gripping arrangements such as, but not limited to, one or more teeth, one or more ribs, one or more rough regions, etc.; however, this is not required. In addition or alternatively, an adhesive (e.g., bone cement, bio-grout, polymer adhesive, etc.) can be used to facilitate in the gripping of the one or more feet of the arms to a portion of the vertebra; however, this is not required. Furthermore, one or more portions of one or more feet can alternatively or additionally be porous and/or include one or more openings or cavities so as to promote bone ingrowth, and thereby facilitate in the gripping of the one or more feet of the arms to a portion of the vertebra; however, this is not required. The one or more porous regions can include one or more materials (e.g., bone, etc.), medication, drugs, etc. to promote and/or inhibit bone growth on one or more regions of the feet; however, this is not required. As can be appreciated, other or additional arrangements can be used to facilitate in the gripping and/or proper operation of the one or more feet of the arms on a portion of the vertebra.

As illustrated in FIGS. 14 and 15, the body section and foot of each arm is formed of a single piece of material. Typically, the material is a metal material; however, other or additional materials can be used. As can be appreciated, the body portion and the foot of one or more arms can be formed of different materials. The body portion and foot of arms 110 and 120 are illustrated as being about the same shape and size. As can be appreciated, the body portion and/or foot of arms 110 and 120 can be the same or different from another arm. The body portion 152 of arm 150 is illustrated as being longer than the body portion of arms 110 and 120; however, this is not required. The foot 154 of arm 150 is illustrated as being about the same size of foot 124 of arm 120; however, this is not required. As such, the body portion and/or foot of the arms can be the same or different from another arm. For instance, the length, profile, thickness and/or cross-sectional shape of the body portion of each arm can be the same or different of the body portion of one or more other arms. Furthermore, the length, profile, thickness and/or cross-sectional shape of the foot of each arm can be the same or different from the foot of one or more other arms. Although not shown, the foot on one or more arms can be designed so as to be connected to the body portion by use of an adhesive, solder, weld, etc.; however, this is not required. As can further be appreciated, the foot can be designed so as to be adjustably oriented relative to the body portion by use of a hinge mechanism, a ratchet mechanism, ball/socket mechanism, etc.; however, this is not required. A set screw and/or other locking arrangement can be used to adjust and/or secure the adjustable foot in place; however, this is not required.

The orientation of arms 110 and 120 relative to one another can be accomplished in a variety of ways. Non-limiting examples of a few ways the two arms can be oriented with respect to each other described and illustrated above with respect to FIGS. 3-8. As can be appreciated, these three arrangements merely illustrate a few of the possible arrangements that can be used to orient and set in position the arms relative to one another. As can be appreciated, the spinal implant can be designed such that one or more of the arms are not adjustable along the longitudinal axis of the spinal implant; however, this is not required. As can also be appreciated, one or more arms can be adjustably oriented in one or more less axes that one or more other arms; however, this is not required. For instance, one or more arms could be adjustably oriented in one or more axes of the spinal implant, and one or more arms could be adjustably oriented in no axis of the spinal implant. In another instance, one or more arms could be adjustably oriented in two or more axes of the spinal implant, and one or more arms could be adjustably oriented in only one axis of the spinal implant. In still another instance, one or more arms could be adjustably oriented in three axes of the spinal implant, and one or more arms could be adjustably oriented in two or one axes of the spinal implant.

Referring again to FIGS. 14 and 15, arm hub 130 includes an arm opening that enables front portions of arms 110, 120 to be at least partially telescopically received in the arm opening. Once arms 110, 120 are positioned on a portion of one or more vertebra, the arms can be set relative to one another. As can be appreciated, many arrangements can be used to set arms 110 and 120 relative to one another (e.g., set screw, set pin, adhesive, adhesive, clamp arrangement, etc.).

Arm hub 130 also includes one or more connection arrangements 136. As illustrated in FIGS. 14 and 15, the connection arrangement 136 is positioned on the top surface of the arm hub. As can be appreciated, the connection arrangement 136 can be located on other regions of the arm hub. Connection arrangement 136 is illustrated as securing the front end 156 to arm hub 130. The front end 156 includes an opening 158 that allow a base portion of connection arrangement 136 to pass through the opening and secure to arm hub 130. The base portion of connection arrangement 136 can be threaded so that the head of the connection arrangement 136 can be tightened onto front end 156 to secure the third arm is position. As can be appreciated, many other or additional arrangements can be used to secure the third arm in position relative to the arm hub. In operation, the third arm can be positioned on the vertebra V prior to, during or after arm 110 and/or arm 120 is secured to the vertebra.

Arm hub 130 can include more than one connection arrangement. The one or more connection arrangements on the arm hub can be designed to connection to a stabilizing system and/or other type of treatment system (e.g., modular heads; one or more attachment sites for rods, plates, and/or medication delivery devices, etc.), and/or connect another arm to the spinal implant several non-limiting configurations of the one or more configurations of the arm hub and/or the one or more configurations of the connection arrangements on the arm hub are described and illustrated in FIGS. 3-13.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to a preferred embodiment. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A spinal implant for connecting to at least a portion of a vertebra comprising an arm hub and first and second arms, each of said first and second arms having first and second ends, said first end of said first and second arms are both securable to said arm hub, said second end of said first arm connected to a foot adapted to engage a portion of vertebra without substantially penetrating into the vertebra, said second end of said second arm connected to a foot adapted to engage a portion of vertebra without substantially penetrating in to the vertebra, said arm hub including an adjustment arrangement and a set mechanism, said adjustment arrangement enabling said first arm to be adjustably positioned relative to said second arm, said adjustment arrangement includes an opening adapted to at least partially telescopically receive said first and second arms, said set mechanism substantially securing said first arm in position relative to said second arm, said set mechanism including an arrangement to at least partially engage at least one of said arms positioned in said adjustment arrangement, said adjustment arrangement designed to enable multi-axis movement and positioning of one or more of said first and second arms in said arm hub such that said first and second arms can lie in a parallel plane or in a non-parallel plane with respect to one another when secured to said arm hub.

2. The spinal implant as defined in claim 1, including a third arm, one end of said third arm connected to a foot adapted to engage a portion of vertebra without substantially penetrating into the vertebra.

3. The spinal implant as defined in claim 2, wherein said third arm is securable to said arm hub.

4. The spinal implant as defined in claim 1, including a connection arrangement adapted to secure to a component of a stabilizing system or other type of treatment system, said connection arrangement positioned on said arm hub.

5. The spinal implant as defined in claim 1, wherein said first end of said first arm includes a first slot formed partially along a longitudinal length of said first arm, said first slot extending at least partially between a top and bottom surface of said arm, said first slot fully extending to said top surface, said bottom surface or combinations thereof, said first slot having first and second inner side walls, said first slot designed to receive a portion of said first end of said second arm when said first and second arms are secured in said arm hub.

6. The spinal implant as defined in claim 5, wherein said first end of said second arm includes a second slot formed partially along a longitudinal length of said second arm, said second slot extending at least partially between a top and bottom surface of said arm, said second slot fully extending to said top surface, said bottom surface or combinations thereof, said second slot having first and second inner side walls, said second slot designed to receive a portion of said first end of said first arm when said first and second arms are secured in said arm hub.

7. The spinal implant as defined in claim 6, wherein said set mechanism designed to engage said at least one of said first and second arms to cause said first end of said second arm to frictionally engage said first slot in said first end of said first arm to thereby fix said relative positions of said first and second arms in said arm hub, said set mechanism including an adjustable contact piece designed to contact at least one outer side wall of said first arm or said second arm when at least one of said first arm and said second arm are at least partially positioned and secured in said arm hub.

8. The spinal implant as defined in claim 6, wherein said set mechanism designed to engage said at least one of said first and second arms to cause said first end of said first arm to frictionally engage said second slot in said first end of said second arm to thereby fix said relative positions of said first and second arms in said arm hub, said set mechanism including an adjustable contact piece designed to contact at least one outer side wall of said first arm or said second arm when at least one of said first arm and said second arm are at least partially positioned and secured in said arm hub.

9. The spinal implant as defined in claim 5, wherein said set mechanism designed to engage said at least one of said first and second arms to cause said first end of said second arm to frictionally engage said first slot in said first end of said first arm to thereby fix said relative positions of said first and second arms in said arm hub, said set mechanism including an adjustable contact piece designed to contact at least one outer side wall of said first arm or said second arm when at least one of said first arm and said second arm are at least partially positioned and secured in said arm hub.

10. A spinal implant for connecting to at least a portion of a vertebra comprising an arm hub and first and second arms, each of said first and second arms having first and second ends, said first end of said first and second arms are both securable to said arm hub, said second end of said first arm connected to a first foot designed to at least partially encircle a pars portion of a vertebra, said second end of said second arm connected to a second foot designed to at least partially encircle pars portion of the same vertebra as said first foot, said first end of said first arm including a first slot formed partially along a longitudinal length of said first arm, said first slot extending at least partially between a top and bottom surface of said arm, said first slot fully extending to said top surface, said bottom surface or combinations thereof, said first slot having first and second inner side walls, said first slot designed to receive a portion of said first end of said second arm when said first and second arms are secured in said arm hub, said second arm including at least one side wall, said at least one side wall of said second arm at least partially facing at least one of said inner side walls of said first slot in said first end of said first arm when said first slot receives said portion of said first end of said second arm, said arm hub including an adjustment arrangement and a set mechanism, said adjustment arrangement enabling said first arm to be adjustably positioned relative to said second arm, said set mechanism designed to secure said first arm in position relative to said second arm, said first and second arms both securable to said arm hub and adjustably positionable in said arm hub, said adjustment arrangement including a first opening designed to at least partially telescopically receive said first arm and a second opening designed to at least partially telescopically receive said second arm, said set mechanism including a contact arrangement to at least partially engage one or both of said first arm and said second arm in said adjustment arrangement so as to at least partially secure one or both of said first arm and said second arm in said arm hub by one or more forces selected from the group consisting of a frictional force and a clamping force, said contact arrangement of said set mechanism including an adjustable contact piece designed to contact at least one outer side wall of said first arm or said second arm when at least one of said first arm and said second arm are at least partially positioned and secured in said arm hub, wherein said at least one outer side wall of said first arm or said second arm is substantially parallel to at least one of said first inner side wall of said first arm, said second inner side wall of said first arm, or said at least one side wall of said second arm.

11. The spinal implant as defined in claim 10, wherein said adjustment arrangement is designed to enable multi-axis positioning of one or both of said first arm and said second arm in said arm hub prior to and after said set mechanism secures one or both of said first arm and said second arm in said arm hub such that said first and second arms can lie in a parallel plane or in a non-parallel plane with respect to one another when secured to said arm hub.

12. The spinal implant as defined in claim 11, wherein said adjustable contact piece is designed to only contact one of said side walls of said first arm and to apply said one or more forces to said side wall of said first arm thereby causing said first arm and said second arm to be secured in said arm hub when said first arm and said second arm are at least partially positioned in said arm hub.

13. The spinal implant as defined in claim 12, wherein in said arm hub includes a stabilizing system connection arrangement designed to secure to a component of a stabilizing system or other type of treatment system.

14. The spinal implant as defined in claim 10, wherein said adjustable contact piece is designed to only contact one of said side walls of said first arm and to apply said one or more forces to said side wall of said first arm thereby causing said first arm and said second arm to be secured in said arm hub when said first arm and said second arm are at least partially positioned in said arm hub.

15. The spinal implant as defined in claim 10, wherein in said arm hub includes a stabilizing system connection arrangement designed to secure to a component of a stabilizing system or other type of treatment system.

16. A spinal implant for connecting to at least a portion of a vertebra comprising an arm hub and first and second arms, each of said first and second arms having first and second ends, said first end of said first and second arms are both securable to said arm hub, said second end of said first arm connected to a foot adapted to engage a portion of vertebra, said second end of said second arm connected to a foot adapted to engage a portion of vertebra, said arm hub including an adjustment arrangement and a set mechanism, said adjustment arrangement enabling said first arm to be adjustably positioned relative to said second arm, said adjustment arrangement includes an opening adapted to at least partially telescopically receive said first and second arms, said set mechanism substantially securing said first arm in position relative to said second arm, said set mechanism including an arrangement to at least partially engage at least one of said arms positioned in said adjustment arrangement to cause at least one of said first and second arms to be secured in said arm hub, said adjustment arrangement designed to enable multi-axis movement and positioning of one or more of said first and second arms in said arm hub such that said first and second arms can lie in a parallel plane or in a non-parallel plane with respect to one another when secured to said arm hub.

17. The spinal implant as defined in claim 16, wherein said set mechanism is designed to cause said first and second arms to frictionally engage another in said adjustment arrangement.

18. The spinal implant as defined in claim 17, wherein said set mechanism is designed to apply a force that is normal to the longitudinal axis of said first or second arms.

19. The spinal implant as defined in claim 18, wherein said first end of said second arm includes a second slot formed partially along said longitudinal axis of said second arm, said second slot having first and second inner side walls, said second slot designed to receive a portion of said first end of said first arm when said first and second arms are secured in said arm hub.

20. The spinal implant as defined in claim 19, including a third arm, one end of said third arm connected to a foot adapted to engage a portion of vertebra.

21. The spinal implant as defined in claim 19, including a connection arrangement adapted to secure to a component of a stabilizing system or other type of treatment system, said connection arrangement positioned on said arm hub.

22. The spinal implant as defined in claim 16, wherein said first end of said second arm includes a second slot formed partially along said longitudinal axis of said second arm, said second slot having first and second inner side walls, said second slot designed to receive a portion of said first end of said first arm when said first and second arms are secured in said arm hub.

23. The spinal implant as defined in claim 16, including a third arm, one end of said third arm connected to a foot adapted to engage a portion of vertebra.

24. The spinal implant as defined in claim 23, wherein said third arm is securable to said arm hub.

25. The spinal implant as defined in claim 16, including a connection arrangement adapted to secure to a component of a stabilizing system or other type of treatment system, said connection arrangement positioned on said atm hub.

* * * * *